US012797198B2

(12) United States Patent
Rister et al.

(10) Patent No.: US 12,797,198 B2
(45) Date of Patent: Nov. 17, 2026

(54) FEMORAL HIP STEM IMPLANT AND CORRESPONDING ORTHOPEDIC BROACH

(71) Applicants: Smith & Nephew, Inc., Memphis, TN (US); Smith & Nephew Orthopaedics AG, Zug (CH); Smith & Nephew Asia Pacific PTE. Limited, Singapore (SG)

(72) Inventors: David W. Rister, Nesbit, MS (US); Mouhsin El-Chafei, Arlington, TN (US); Marc Wright, Memphis, TN (US); Kara McCluskey, Memphis, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 338 days.

(21) Appl. No.: 18/685,093

(22) PCT Filed: Aug. 19, 2022

(86) PCT No.: PCT/US2022/040849
§ 371 (c)(1),
(2) Date: Feb. 20, 2024

(87) PCT Pub. No.: WO2023/027952
PCT Pub. Date: Mar. 2, 2023

(65) Prior Publication Data
US 2024/0341977 A1 Oct. 17, 2024

Related U.S. Application Data

(60) Provisional application No. 63/235,858, filed on Aug. 23, 2021.

(51) Int. Cl.
*A61F 2/36* (2006.01)
*A61B 17/16* (2006.01)
*A61F 2/30* (2006.01)

(52) U.S. Cl.
CPC .......... *A61F 2/3662* (2013.01); *A61B 17/164* (2013.01); *A61F 2002/30822* (2013.01);
(Continued)

(58) Field of Classification Search
CPC .. A61F 2/32; A61F 2/3662; A61F 2002/3082; A61F 2002/30822;
(Continued)

(56) References Cited

U.S. PATENT DOCUMENTS 5,665,091 A * 9/1997 Noble ................ A61B 17/1659 606/85
6,887,278 B2 5/2005 Lewallen
(Continued)

FOREIGN PATENT DOCUMENTS

EP 1216668 A2 6/2002
EP 1216668 A3 1/2004
(Continued)

OTHER PUBLICATIONS

European Patent Office, European Search Report, dated Nov. 28, 2024, 17 pages.
(Continued)

*Primary Examiner* — Melanie R Tyson
(74) *Attorney, Agent, or Firm* — KDW Firm PLLC

(57) ABSTRACT

Orthopaedic implants and corresponding instrumentation are disclosed. More particularly, a femoral implant and a corresponding broach are presented for surgically repairing a hip joint. The femoral implant includes an elongated stem configured to be inserted within an intramedullary canal of a patient's femur. The femoral implant configured to maxi-
(Continued)

mize "fit" within the intramedullary canal. The orthopedic broach may include differential tooth patterns. For example, the broach may include first, second, and third separate and unique tooth patterns. In use, the various tooth patterns are located in specific locations on the broach to achieve a specific purpose to thereby optimize engagement between the patient's intramedullary canal and the femoral implant. In various embodiments, the broach is specifically matched to mimic the femoral implant, and specifically the teeth (compaction teeth) formed on the proximal region of the broach are matched to the porous coating formed on the implant.

20 Claims, 31 Drawing Sheets

(52) U.S. Cl.
CPC ............... *A61F 2002/30828* (2013.01); *A61F 2002/30904* (2013.01)

(58) Field of Classification Search
CPC .. A61F 2002/30827; A61F 2002/30828; A61F 2002/30904; A61B 17/164; A61B 17/1664
See application file for complete search history.

(56) References Cited

U.S. PATENT DOCUMENTS

| | | | |
|---|---|---|---|
| 6,974,482 B2 | 12/2005 | Zhu | |
| 7,060,102 B2 | 6/2006 | Thompson | |
| 7,175,668 B2 | 2/2007 | Zweymuller | |
| 7,214,246 B2 | 5/2007 | Serbousek | |
| 7,481,842 B2 | 1/2009 | Noetzli | |
| 7,494,509 B1 | 2/2009 | Hershberger | |
| 7,857,859 B2 | 12/2010 | Willi | |
| 8,252,062 B2 | 8/2012 | Bandoh | |
| 8,480,756 B2 | 7/2013 | Frederick | |
| 8,764,846 B2 | 7/2014 | Grappiolo | |
| 8,936,649 B2 | 1/2015 | Huff | |
| 9,192,477 B2 | 11/2015 | Slater | |
| 9,351,841 B2 | 5/2016 | Meier | |
| 9,358,115 B2 | 6/2016 | Slater | |
| 9,381,086 B2 | 7/2016 | Ries | |
| 9,750,850 B2 | 9/2017 | Fonte | |
| 10,405,984 B2 | 9/2019 | McMinn | |
| 10,426,623 B2 | 10/2019 | Fridshtand | |
| 10,842,915 B2 | 11/2020 | Morrey | |
| 11,259,932 B2 | 3/2022 | Piecuch | |
| 11,351,034 B2 | 6/2022 | Satterthwaite | |
| 2002/0177900 A1* | 11/2002 | Serbousek | A61F 2/30771 623/23.31 |
| 2002/0177901 A1 | 11/2002 | Howie | |
| 2004/0138756 A1* | 7/2004 | Reeder | A61B 17/15 623/21.11 |
| 2006/0184250 A1 | 8/2006 | Bandoh | |
| 2010/0228356 A1 | 9/2010 | Frederick et al. | |
| 2012/0265319 A1 | 10/2012 | Prybyla | |
| 2013/0197866 A1 | 8/2013 | Wuestemann et al. | |
| 2014/0094925 A1 | 4/2014 | Huff | |
| 2014/0303742 A1 | 10/2014 | Prybyla | |
| 2014/0343685 A1 | 11/2014 | Ranawat | |
| 2017/0086981 A1 | 3/2017 | Bailey | |
| 2019/0099191 A1 | 4/2019 | Huff | |
| 2021/0137688 A1 | 5/2021 | Biggs | |
| 2022/0117745 A1 | 4/2022 | Roy | |
| 2022/0249140 A1 | 8/2022 | Favre | |
| 2023/0157709 A1 | 5/2023 | Gerges | |

FOREIGN PATENT DOCUMENTS

| | | |
|---|---|---|
| EP | 1429691 B1 | 6/2008 |
| EP | 2708193 A1 | 3/2014 |
| EP | 2386273 B1 | 3/2016 |
| EP | 3295899 B1 | 4/2019 |
| EP | 3244837 B1 | 6/2019 |
| EP | 3714841 B1 | 3/2022 |
| FR | 2851456 A1 | 8/2004 |
| FR | 2961684 A1 | 12/2011 |
| JP | 2002291778 A | 10/2002 |
| KR | 102168618 B1 | 10/2020 |

OTHER PUBLICATIONS

Smith & Nephew, "Polarstem Cementless Stem System," 00766 V2 May 2015, 2015, 4 pages.
Smith & Nephew, "Anthology Primary Hip System," Innovative by design, 45860504 Jan. 2007, 2007, 4 pages.
Smith & Nephew, "Polarstem Cementless and Cemented Stem System," Surgical Technique, 01217-en V5 0917, 2017, 32 pages.
Smith & Nephew, "Synergy Cementless Stem," Surgical Technique, 45610101 7138-0349 Nov. 2004, 2004, 32 pages.
Smith & Nephew, "Anthology Primary Hip System," Surgical Technique, 71381440 REV0 Aug. 2010, 2010, 28 pages.
Stryker, "Insignia Hip Stem," Data driven design aligned to your approach, INSIGN-PG-1_31966, 2021, 8 pages.
DePuy Synthes, "ACTIS Total Hip System," Surgical Technique, 160929-201130 EMEA, 2016, 20 pages.
Zimmer Biomet, "Avenir® Femoral Hip System," 0725.1-GLBL-en-REV1016, 2016, 12 pages.
Smith & Nephew, "Polarstem Cementless and CementedStem System," Surgical Technique, 01217-en (1513) V4 Jan. 2016, 2016, 32 pages.
Johanna Bätz et al., "The influence of broach design on bone friction and osseodensification in total hip arthroplasty," Clinical Biomechanics 73 (2020), Dec. 2019, 234-240.
Andrew Jacobs, BS et al., "The effects of femoral stem misalignment and how next generation implant systems can help improve postperative outcomes," 2022, 15 pages.
International Search Report and Written Opinion for International Application No. PCT/US2022/040849, filed on Aug. 19, 2022, 9 pages.
European Patent Office, European Search Report, dated Oct. 13, 2025, 11 pages.

* cited by examiner

FEMORAL HIP STEM IMPLANT AND CORRESPONDING ORTHOPEDIC BROACH

CROSS-REFERENCE TO RELATED APPLICATIONS

This application is a National Phase filing of International Application No. PCT/US2022/040849, filed Aug. 19, 2022, which application is a non-provisional of, and claims the benefit of the filing date of, U.S. provisional patent application No. 63/235,858, filed Aug. 23, 2021, entitled "Femoral Hip Stem Implant" the entirety of which application is incorporated by reference herein.

FIELD OF THE DISCLOSURE

The present disclosure relates generally to orthopedic devices and instruments, and more particularly to a femoral hip stem implant including one or more features, geometries, and/or dimensions to optimize (e.g., maximize) fit within a greater population of patients and/or an orthopedic broach for preparing a patient's intramedullary canal to receive the femoral hip stem implant.

BACKGROUND OF THE DISCLOSURE

Orthopedic implants are well known and commonplace in today's society. Orthopedic implants may be used, for example, to stabilize an injury, to support a bone fracture, to fuse a joint, and/or to correct a deformity. Orthopedic implants may be attached permanently or temporarily, and may be attached to the bone at various locations, including implanted within a canal or other cavity of the bone, implanted beneath soft tissue and attached to an exterior surface of the bone, or disposed externally and attached by fasteners such as screws, pins, and/or wires. Some orthopedic implants allow the position and/or orientation of two or more bone pieces, or two or more bones, to be adjusted relative to one another.

One such orthopedic implant is a femoral hip stem implant used to repair a hip joint. The hip joint is a frequent place for joint damage and/or injury. Femoral hip stem implants can be implanted or otherwise associated with the bony anatomy for treating traumatic injuries, reconstructing joint function, or for other purposes. Femoral hip stem implants may include an elongated insertion region, such as a stem region, which can be at least partially inserted into an intramedullary canal of a patient's proximal femur.

In some instances, the success of the femoral hip stem implant is dependent on how well the elongated insertion region fits into the patient's bony anatomy (e.g., intramedullary canal of the patient's femur). For example, it is important that proximal portions of the elongated insertion region of the femoral hip stem implant fit tightly into the intramedullary canal (e.g., creating a press-fit between the proximal region of the implant and the inner surface of the intramedullary canal of the patient's femur), such that the stem loads proximal portions of the patient's femur, preventing bone loss through stress shielding and/or resorption (and potentially subsequent failure of the implant). It is also important that distal portions are properly positioned within the intramedullary canal; however, the fit should not be so tight as to prevent proximal loading.

A good fit between the femoral hip stem implant and its associated bony anatomy may also help to prevent or lessen micromotion between the implant and the bone. Excessive micromotion may also lead to implant failure.

Because bone geometries vary from person to person (and may also vary with age), typical orthopaedic implants are often offered as part of a set, a kit, or series of different sized implants. Typically, implant sets are created by first designing one size of implant and then scaling that implant in a proportional manner to define the geometries of the other implant sizes (e.g., increasing the width of the elongated insertion region by a uniform amount along the entire length of the stem).

Typical implant system growth does not accurately reflect the geometries of different bone sizes. Larger femurs, for example, are not simply bigger versions of smaller femurs. For instance, it has been discovered that proximal portions of the patient's intramedullary canal (some or all of which may be referred to as the metaphysis) may "grow" at a greater rate than distal portions (some or all of which may be referred to as the diaphysis) as femoral size increases. Thus, femoral hip stem implant sets that grow the proximal portion at the same rate as the distal portion from size to size do not necessarily reflect the actual geometries of the various sizes of femurs. Thus, implant sets made in accordance with traditional methodologies may, in some cases, fit poorly when implanted, and may lead to implant failure for the reasons discussed above or for other reasons.

Moreover, when implanting a femoral hip stem implant, proper preparation of the patient's intramedullary canal for receiving the femoral hip stem implant is important. As a result, orthopedic instruments such as, for example, broaches, have been developed. In use, a broach is used during, for example, hip arthroplasty surgeries. In use, the surgeon uses the broach to prepare an inner surface of a patient's intramedullary canal to receive the femoral hip stem implant. The preparation of the intramedullary canal by the surgeon is designed to insure a proper fit between the patient's femur and the hip stem implant.

Implantation of hip stem implants require accurate preparation of the bone or intramedullary canal in order to guarantee good contact between the hip stem implant and the patient's bone. Generally speaking, reducing the gaps or spaces between the hip stem implant and the patient's bone (e.g., between the outer surface of the implant and the inner surface of the intramedullary canal), while ensuring adequate stem contact in key areas of the intramedullary canal in anterior/posterior and medial/lateral directions improves initial stability and long-term bone ingrowth/fixation.

The intramedullary canal of the patient's bone (e.g., femur) may be prepared for implantation of the hip stem implant by broaching and reaming a resected end of the proximal femur. In use, the intramedullary canal of the patient's femur can be prepared using a broach to provide a seat for the hip stem implant. Generally speaking, a broach is a cutting tool, which may be moved or manipulated in an axial direction to create, enlarge, prepare, etc. the cavity or intramedullary canal of the patient's bone. A broach can be used to create a cavity with a noncircular cross-section. It is suitable for preparing a portion of the intramedullary cavity that receives the hip stem implant, in particular to ensure that the tapered shape of the hip stem implant, which can be a complicated irregular shape, is properly matched by the shape of the inner surface of the patient's intramedullary canal. As will be appreciated by one of ordinary skill in the art, in use, with the head of the patient's femur removed, the broach can be inserted into the intramedullary canal of the femur. Cancellous bone, which is softer and somewhat spongy, surrounds the intramedullary canal. Surrounding the cancellous bone is cortical bone, which is stronger. In use, the broach can be used to cut into the bone.

Improper bone cavity preparation can lead to loosening of the hip stem implant over time (e.g., proximally fixed hip stem implants may loosen over time if bony fixation with the implant occurs away from the intended fixation regions on the hip stem implant). To further complicate matters, recent developments in hip stem implants has resulted in hip stem implants that include coated and non-coated sections of the hip stem implant.

Thus, it would be beneficial to provide a femoral hip stem implant or set of implants that optimizes (e.g., maximizes) fit. In addition, it would be beneficial to provide an improved orthopedic broach that better matches the shape and design of the subsequently implanted femoral hip stem implant. In addition, there remains a need for an improved broach that avoids, or at least minimizes, distal fixation of proximally coated femoral hip stem implants. The present invention satisfies these needs and provides other benefits and advantages in a novel and unobvious manner.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure illustrates and describes various embodiments of a femoral hip stem implant. In some embodiments, the femoral hip stem implant includes a neck region and an elongated insertion region or stem. The elongated insertion region or stem includes a proximal region and a distal region. The femoral hip stem implant includes an upper portion or shoulder, a neck extending from the shoulder, and a distal tip. In addition, the femoral hip stem implant also includes a medial surface or side, a lateral surface or side, an anterior surface or side, and a posterior surface or side. In various embodiments, the femoral hip stem implant includes one or more features, geometries, and/or dimensions to optimize (e.g., maximize) fit within a greater population of patients.

In addition, the femoral hip stem implant may be configured to be surgical approach agnostic. That is, the femoral hip stem implant may be configured to allow surgeons to insert the femoral hip stem implant using any approach of their choosing. For example, the femoral hip stem implant may include one or more features, geometries, and/or dimensions to facilitate a direct anterior surgical approach. In use, an anterior approach is often preferred by various surgeons since it provides the most direct access to the anterior aspects of the patient's hip. In addition, a direct anterior approach eliminates, or at least minimizes, dissection of muscles thereby providing improved recovery time.

In some embodiments, the femoral hip stem implant is configured as a collarless stem. Alternatively, in some embodiments, the femoral hip stem implant includes a collar.

In some embodiments, the upper portion or shoulder may be flat, or define a substantially flat surface.

In some embodiments, the femoral hip stem implant may be configured with a standard neck configuration. Alternatively, in some embodiments, the femoral hip stem implant may be configured with a high offset configuration.

In some embodiments, the elongated insertion region or stem of the femoral hip stem implant may include an anterior-posterior taper. That is, in some embodiments, the anterior and posterior surfaces or sides of the implant taper inwardly toward a central longitudinal axis of the implant. Thus arranged, the distal region of the femoral hip stem implant may include an anterior-posterior taper and a medial-lateral taper.

In some embodiments, the implant includes a dual-tapered anterior-posterior taper arrangement. Thus arranged, the implant includes a first anterior-posterior taper extending from a shoulder to a transition point and a second anterior-posterior taper extending from the transition point towards the distal tip, the second anterior-posterior taper being different than the first anterior-posterior taper.

In some embodiments, when provided in a system or kit, as the length of the femoral hip stem implant increases, the anterior-posterior taper decreases.

In some embodiments, the medial side of the proximal region of the hip stem implant includes a constant arc of curvature configured to provide a press-fit against the inner surface of the intramedullary canal in use.

In some embodiments, the proximal region of the hip stem implant includes, and is defined by, a porous coated or roughened surface or region (terms used interchangeably herein) formed thereon. Thus arranged, the implant may include a porous coated region and a non-coated region. In addition, the proximal region may include a plurality of grooves formed on the anterior and posterior sides of the femoral hip stem implant. The grooves may be angled downwards from the lateral side toward the medial side (grooves extending at an angle relative to a longitudinal axis of the implant). In addition, the grooves, at least those formed on the anterior side, may wrap around a corner of the implant (e.g., the grooves may wrap around the medial blend radius of the implant from the anterior-posterior aspect to the medial aspect of the stem) and extend partially along the medial side thereof.

In accordance with one or more features of the present disclosure, an improved orthopedic broach is also disclosed. In various embodiments, the orthopedic broach is provided as part of, or operatively associated with, a system or a kit along with a subsequently implanted hip stem implant such as, for example, the femoral hip stem implant described herein. In use, the broach is arranged and configured to avoid, or at least minimize, distal fixation of the hip stem implant within the patient's intramedullary canal. In addition, the broach includes a proximal region that is arranged and configured to mimic or match the proximal region of the hip stem implant to optimize preparation of the intramedullary canal so that a desired press-fit is achieved between the proximal region of the hip stem implant and the inner surface of the patient's intramedullary canal.

In some embodiments, the broach includes a differential tooth pattern. That is, the broach includes a plurality of tooth patterns such as, for example, first, second, and third tooth patterns wherein each of the tooth patterns is different or unique from the other tooth patterns. In use, the various tooth patterns are arranged and configured in specific locations on the broach to achieve a specific purpose, namely, to optimize the remaining bone within the patient's intramedullary canal to facilitate improved engagement with the subsequently implanted hip stem implant, in particular with respect to the proximally formed porous coated surfaces and anterior-posterior grooves formed on the anterior and posterior sides of the proximal region of the hip stem implant.

For example, in one preferred embodiment, the broach includes a distal region and a proximal region. The distal region including a first tooth pattern arranged and configured as extraction teeth to cut or remove the patient's bone to avoid, or at least minimize, distal fixation of the subsequently implanted hip stem implant. That is, in use, the first tooth pattern (e.g., extraction teeth) formed on the distal region of the broach are arranged and configured to penetrate into and remove any bone that they come into contact with to create an envelope to facilitate proper positioning of the distal region while avoiding bony fixation of the distal region of the subsequently implanted hip stem implant within the intramedullary canal (e.g., to produce an envelope that minimizes or avoids press fit of the distal aspect or region of the femoral hip stem implant within the intramedullary canal to create a preferential press fit in the proximal portion of the femoral hip stem implant in the region corresponding to the anterior—posterior grooves and porous coated region).

In addition, the proximal region of the broach includes a second tooth pattern on the anterior, posterior, medial and lateral sides thereof. The second tooth pattern being arranged and configured to compact, as opposed to removing, the patient's bone (e.g., compaction teeth are configured to leave larger particles of bone at the boney interface with greater penetration and densification of local boney tissue). In addition, the second tooth pattern may be arranged horizontally so that the second tooth pattern is angled relative to the anterior and posterior grooves formed on the anterior and posterior sides of the subsequently implanted hip stem implant. Moreover, the proximal region of the broach is arranged and configured to mimic and/or match the coated/uncoated sections of the proximal region of the subsequently implanted hip stem implant to address the interface between the anterior and posterior sides of the hip stem implant and the patient's bone (cortical/cancellous). That is, the shape and location (e.g., dimensions) of the proximal region (e.g., second and third teeth patterns) of the broach are arranged and configured to mimic and/or match the coated proximal region of the subsequently implanted hip stem implant. Lastly, the proximal region may include a third tooth pattern formed on the anteromedial, anterolateral, posteromedial and posterolateral aspects thereof. In use, the third tooth pattern may be arranged as horizontal teeth with an angled "cutting flute" relief passing through for effective removal of boney residue intended to preferentially achieve press fit away from the adjacent bone at the "corners" of the broach where anterior, posterior, medial and lateral bone of greater surface density to achieve an optimized or preferential press fit in the corresponding region of the hip stem implant.

In various embodiments, a system or kit including a hip stem implant and an orthopedic broach used to prepare a patient's intramedullary canal for receipt of the hip stem implant is disclosed. The hip stem implant includes a proximal region, a distal region, an anterior side, a posterior side, a medial side, and a lateral side. In various embodiments, the proximal region includes a porous coated and/or roughened surface or region including a plurality of grooves formed on the anterior and posterior sides of the porous and/or roughened coated surface. The grooves being angled downwards from the lateral side toward the medial side (grooves extending at an angle relative to a longitudinal axis of the implant).

The broach includes a proximal region, a distal region, an anterior side, a posterior side, a medial side, and a lateral side. The broach including an outer surface having a size and shape substantially similar to an outer surface of the hip stem implant. The broach including differential teeth or tooth patterns formed thereon. In one preferred embodiment, the broach includes three different types of teeth including extraction or cutting teeth (e.g., diamond teeth), compaction teeth (e.g., annular teeth), and proximal-lateral teeth (e.g., annular teeth with interrupted cuts).

In various embodiments, the proximal region of the broach includes compaction teeth (e.g., teeth arranged and configured to compact the bone on the inner surface of the intramedullary canal as opposed to cutting into it or removing it) formed on the anterior and posterior surfaces thereof. In various embodiments, the positioning and layout of the compaction teeth mimics or matches the configuration and layout of the porous coated and/or roughened region formed on the hip stem implant (e.g., the proximal region formed on the broach including the compaction teeth has a shape and location (e.g., dimensions) that substantially matches or mimics the same shape and location (e.g., distance) of the porous coated region formed on the proximal region of the hip stem implant). In addition, the compaction teeth formed on the anterior and posterior sides of the broach are arranged and configured to extend horizontally (e.g., teeth extend perpendicularly relative to a longitudinal axis of the broach). Thus arranged, the broach is arranged and configured to form horizontal parallel ridges on the inner surface of the patient's intramedullary canal, the ridges being angled relative to the grooves formed on the anterior and posterior sides of the subsequently implanted hip stem implant.

In some embodiments, the compaction teeth are arranged and configured as annular teeth extending horizontally from the lateral side to the medial side of the broach.

In some embodiments, the distal region of the broach includes a first set of extraction teeth arranged and configured to cut or remove the patient's bone.

In some embodiments, the first or extraction teeth extend circumferentially about the distal region of the broach (e.g., first or extraction teeth are formed on the anterior, posterior, medial, and lateral surfaces of the distal region of the broach).

In some embodiments, the first or extraction teeth are arranged and configured as diamond or pyramid shaped teeth.

In some embodiments, the medial and lateral sides of the proximal region of the broach include a third set of teeth having a third tooth pattern. The third set of teeth being arranged and configured as extraction teeth (e.g., third set of teeth are configured to form or define interrupted cuts along edges of the medial and lateral broach to remove any bone to prevent lateralization of the broach). That is, the proximal region of the broach may include a third set of teeth having a third tooth patten formed on the anteromedial, anterolateral, posteromedial and posterolateral aspects thereof. In use, location of the third tooth pattern is arranged and configured to correspond to the proximal press-fit section of the same-sized femoral stem in the antero- and posteromedial and lateral aspects.

In some embodiments, the broach includes a connection mechanism arranged and configured to enable the broach to be coupled to a handle, an orthopedic impactor, etc. In some embodiments, the connection mechanism is a female component such as, for example, a cavity or a pocket, to prevent interference with subsequent preparation of a patient's acetabular.

Embodiments of the present disclosure provide numerous advantages. For example, by utilizing a femoral hip stem implant in accordance with features, geometries, and/or dimensions of the present disclosure an improved fit with the patient's intramedullary canal can be expected for a larger number of patients within the population. In addition, and/or alternatively, by providing a system including an orthopedic broach that is configured to match and/or mimic the subsequently implanted femoral hip stem implant, the broach can be optimized to prepare the patient's intramedullary canal to facilitate improved engagement with the subsequently implanted femoral hip stem implant, especially as it pertains to long-term bony on-growth with the anterior-posterior grooves and porous coated proximal region of the hip stem implant. The broach enables cancellous bone to be removed or compacted in the subsequent proximal and distal opposing surfaces of the hip stem implant by enabling distal and mid body rasping of the cortices and proximal compaction of cancellous bone. In addition, the distal region of the broach can be configured to prepare the distal portion of the patient's femur through the mid body of the hip stem implant to enable improved proximal engagement without risking mid body potting (e.g., the distal region of the broach can be configured to extract a slightly larger distal portion of the patient's femur via rasping or scraping). Thereby, facilitating an improved press fit engagement between the proximal region of the implant and the patient's prepared bone while avoiding, or at least minimizing, distal fixation.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, specific embodiments of the disclosed device will now be described, with reference to the accompanying drawings, in which.

Figure 1A:
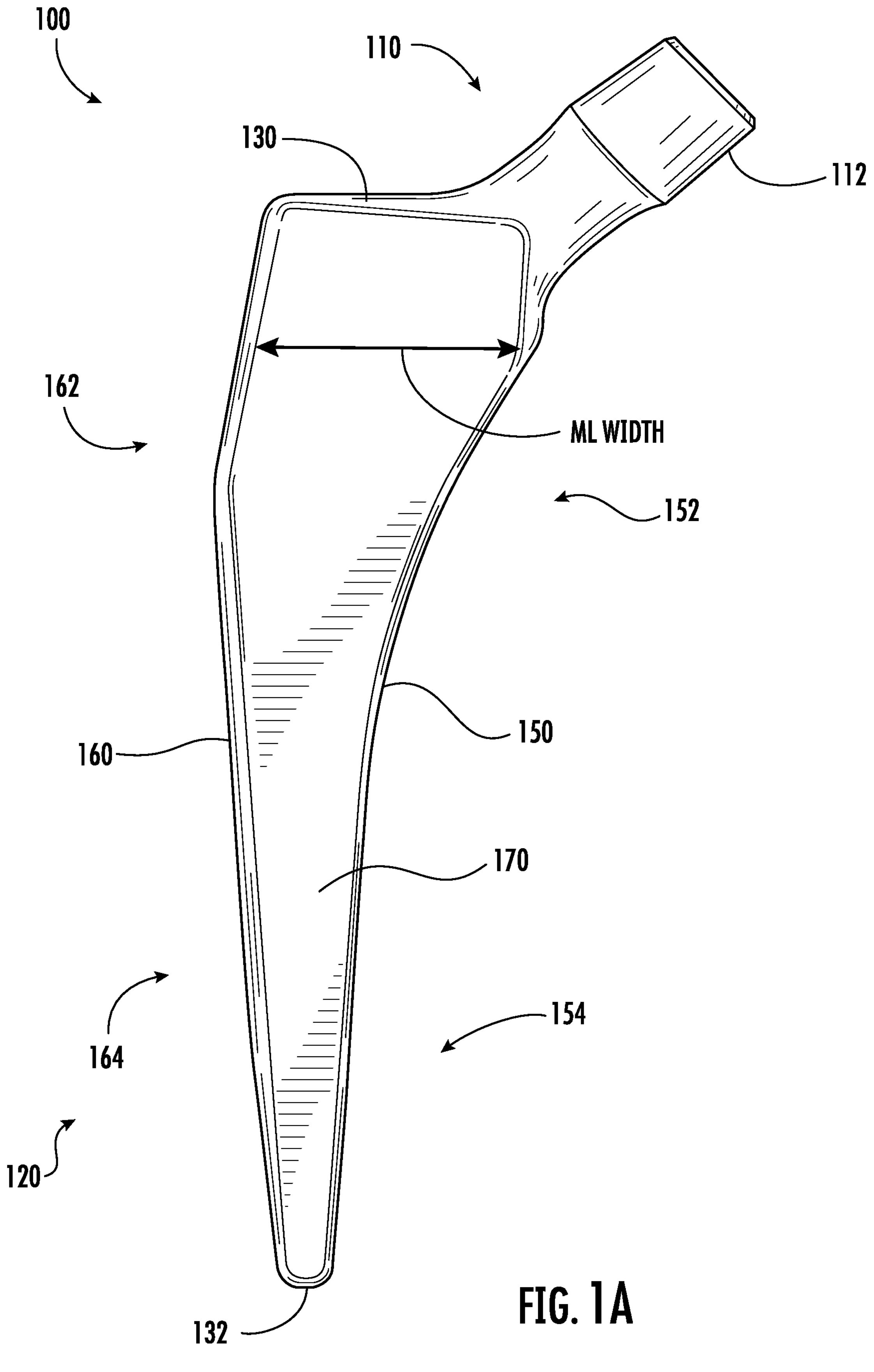
FIG. 1A illustrates a frontal (anterior) view of an embodiment of a femoral hip stem implant in accordance with one or more features, geometries, and/or dimensions of the present disclosure.

The drawings are not necessarily to scale. The drawings are merely representations, not intended to portray specific parameters of the disclosure. The drawings are intended to depict various embodiments of the disclosure, and therefore are not to be considered as limiting in scope. In the drawings, like numbering represents like elements.

DETAILED DESCRIPTION

Various features or the like of orthopedic implants, instruments, and corresponding systems will now be described more fully hereinafter with reference to the accompanying drawings, in which one or more features of the orthopedic implants, instruments, and corresponding systems will be shown and described. In some embodiments, various features, geometries, and/or dimensions of a femoral hip stem implant, a hip stem implant, a femoral implant, an implant, etc. (terms used interchangeably herein without the intent to limit or distinguish) or a set of femoral hip stem implants will now be described more fully herein with reference to the accompanying drawings, in which one or more features, geometries, and/or dimensions of the femoral hip stem implant will be shown and described. In addition, and/or alternatively, various features or the like of orthopedic instruments such as, for example, an orthopedic broach, will now be described more fully herein with reference to the accompanying drawings, in which one or more features of the broach will be shown and described. It should be appreciated that the various features of the femoral hip stem implant and orthopedic broach may be used independently of, or in combination, with each other. It will be appreciated that a femoral hip stem implant and/or broach as disclosed herein may be embodied in many different forms and may selectively include one or more features, geometries, and/or dimensions described herein. As such, the femoral hip stem implant and/or broach should not be construed as being limited to the specific embodiments set forth herein. Rather, these embodiments are provided so that this disclosure will convey certain features, geometries, and/or dimensions to those skilled in the art.

As will be described in greater detail herein, in accordance with one or more features, geometries, and/or dimensions of the present disclosure, the femoral hip stem implant is arranged and configured to be implanted within an intramedullary canal of a patient's femur adjacent to the proximal end of the femur. In use, the femoral hip stem implant includes one or more features, geometries, and/or dimensions to optimize (e.g., maximize) fit within a greater population of patients. In addition, the femoral hip stem implant includes one or more features arranged and configured to ensure improve short-term and long-term fixation within the intramedullary canal of the patient's femur.

In addition, and/or alternatively, in accordance with one or more features of the present disclosure, an orthopedic broach arranged and configured to optimize removal and/or preparation of the patient's bone to facilitate improved engagement with a subsequently implanted orthopedic implant such as, for example, the femoral hip stem implant, will be shown and described.

In some embodiments, the orthopedic broach includes a body having a differential tooth pattern. That is, in some embodiments, the broach includes different teeth patterns arranged and configured to prepare the patient's bone. For example, in some embodiments, the broach includes first, second, and third different teeth patterns. In use, as will be described in greater detail herein, the broach includes a proximal region and a distal region. In addition, the broach includes medial and lateral sides, and anterior and posterior sides. In some embodiments, the distal region includes extraction teeth such as, for example, diamond shaped teeth, arranged and configured to optimize reaming of the intramedullary canal (e.g., diamond shaped teeth arranged and configured to remove any bone that the leading distal end of the broach comes into contact with to facilitate easier insertion of the subsequent hip stem implant and to produce an envelope that minimizes or avoids press fit of the distal aspect ore region of the femoral hip stem implant within the intramedullary canal to create a preferential press fit in the proximal portion of the femoral hip stem implant in the region corresponding to the anterior-posterior grooves and porous coated region.

In addition, the anterior, posterior, medial and lateral sides of the proximal region of the broach include a second tooth pattern arranged and configured to compact and/or rake (as opposed to removing or extracting the patient's bone) the corresponding inner surface of the patient's intramedullary canal to optimize engagement with the anterior and posterior grooves formed on the hip stem implant and/or the porous coated and/or roughened surface formed on the hip stem implant. In addition, the medial and lateral sides (e.g., anteromedial, anterolateral, posteromedial and posterolateral aspects) of the broach include a third tooth pattern arranged and configured to extract any bone of the patient's intramedullary canal to promote improved clearance and/or to prevent lateralization.

In accordance with one or more features of the present disclosure, a system and/or kit is provided including one or more femoral hip stem implants and one or more orthopedic broaches wherein the orthopedic broach is matched to the femoral hip stem implant. That is, in accordance with one or more features of the present disclosure, the proximal region formed on the broach including the compaction teeth formed thereon has a shape and location (e.g., dimensions) that substantially matches or mimics the shape and location (e.g., dimension) of the porous coated and/or roughened region formed on the proximal region of the hip stem implant. Thus arranged, the proximal region of the broach mimics or matches the porous coated and/or roughened region of the hip stem implant (e.g., placement of the compaction teeth on the broach mimics or matches placement of the porous coated and/or roughened region on the hip stem implant to facilitate improved long-term stability by facilitating improved bony on-growth).

Figure 1B:
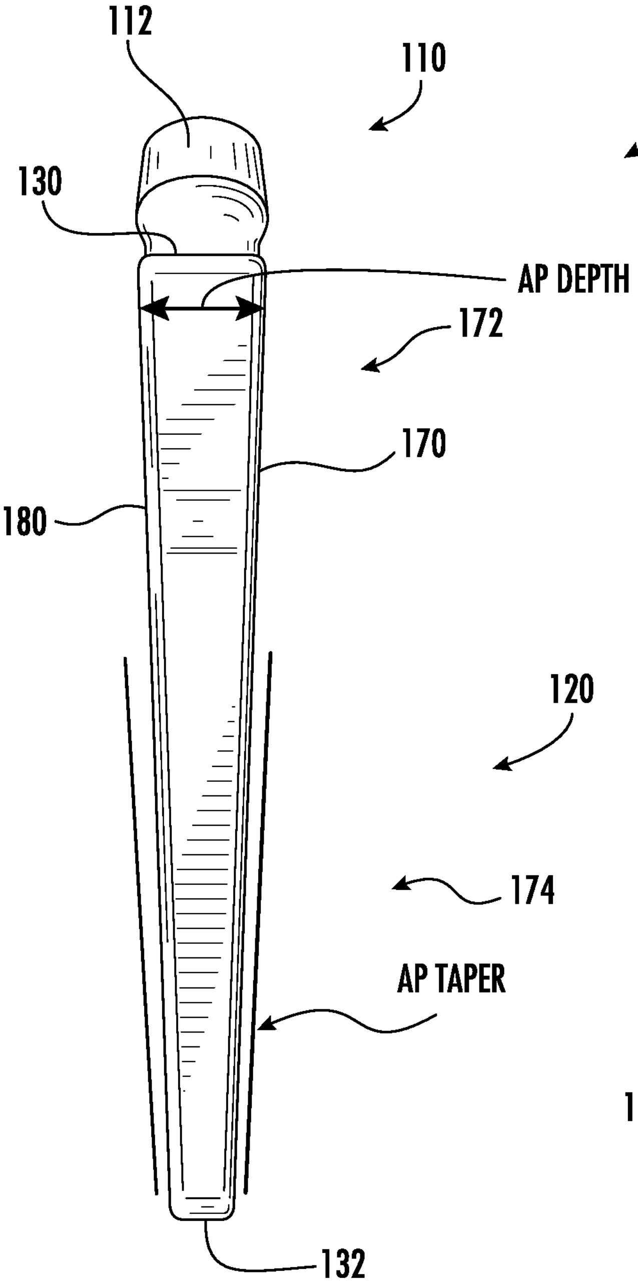
FIG. 1B illustrates a side (lateral) view of the femoral hip stem implant shown in FIG. 1A.
Figure 1C:
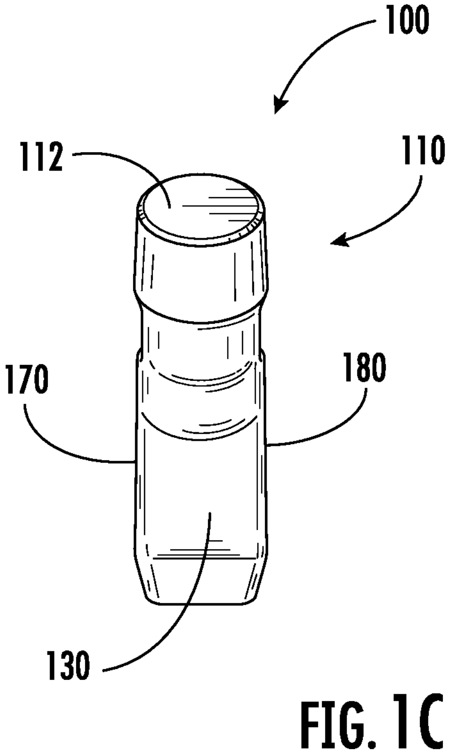
FIG. 1C illustrates a top (superior) view of the femoral hip stem implant shown in FIG. 1C.
Figure 2C:
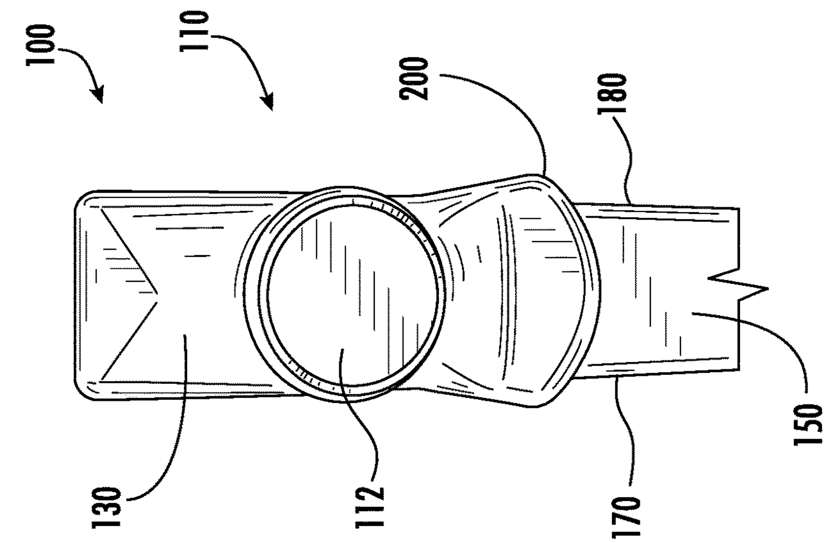
FIG. 2C illustrates a top (superior) view of the femoral hip stem implant shown in FIG. 2C.
Figure 2B:
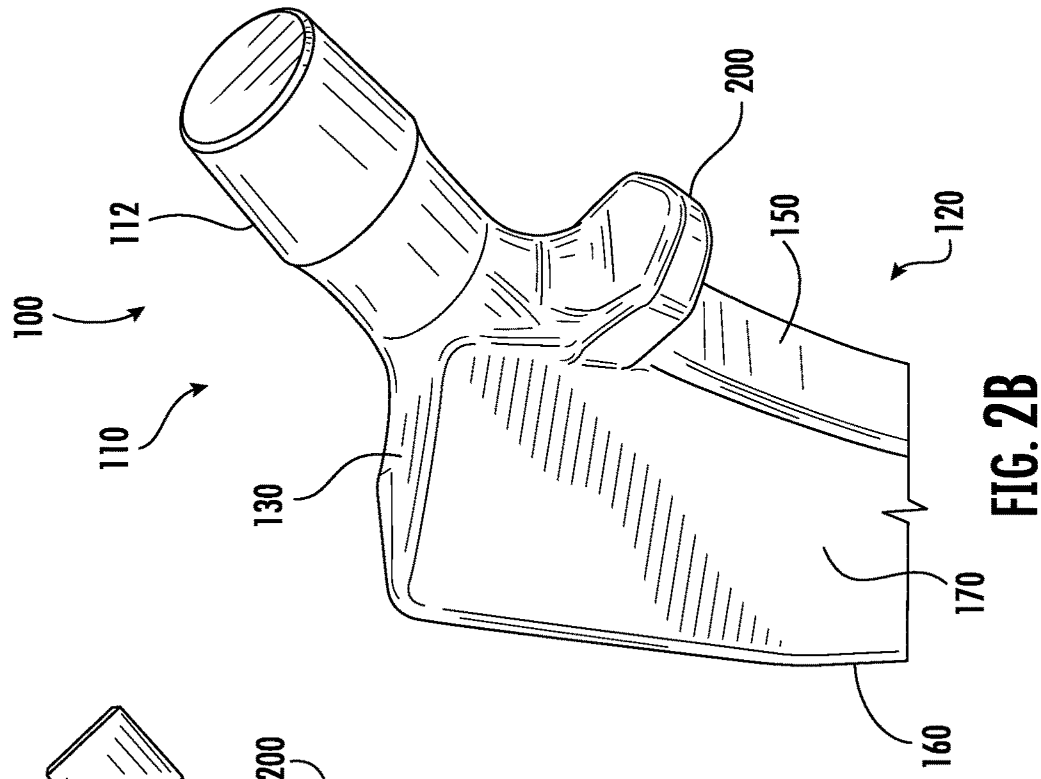
FIG. 2B illustrates an isometric side view of the femoral hip stem implant shown in FIG. 2A.
Figure 2A:
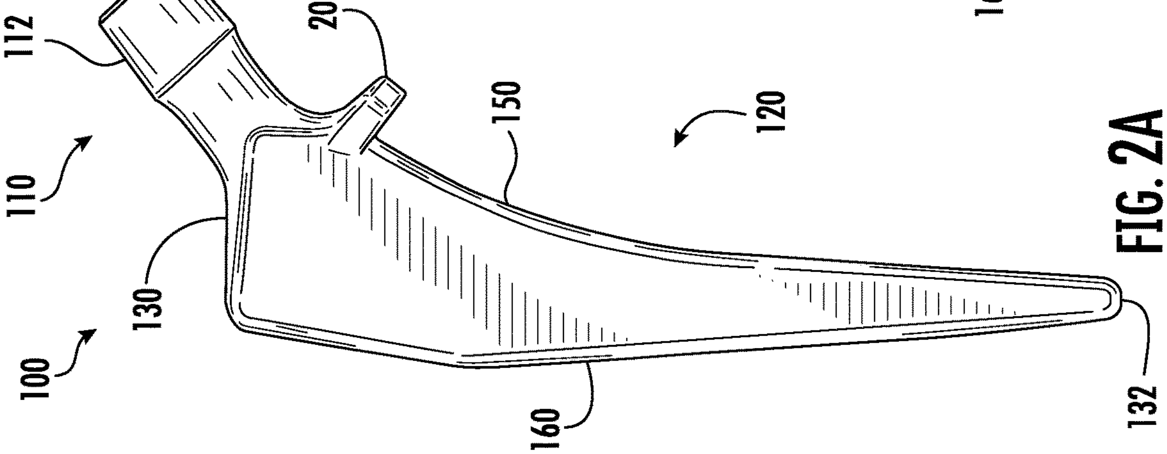
FIG. 2A illustrates a frontal (anterior) view of an alternate embodiment of a femoral hip stem implant in accordance with one or more features, geometries, and/or dimensions of the present disclosure.

Referring to FIGS. 1A-1C, an embodiment of an orthopaedic femoral hip implant 100 in accordance with one or more features of the present disclosure is shown. As shown, the femoral hip implant 100 includes a neck region 110 and an elongated insertion region or stem 120. The neck region 110 including a neck 112. As illustrated, the femoral hip implant 100 may be arranged as a collarless stem, although as illustrated in FIGS. 2A-2C, the femoral hip implant 100 may include a collar 200.

As will be appreciated by one of ordinary skill in the art, in use, the patient's femur is initially prepared for implantation of the femoral hip implant 100 by, for example, resecting the proximal femur and broaching the intramedullary canal in the patient's femur. The femoral hip implant 100 is then inserted into the intramedullary canal of the prepared femur. In use, the elongated insertion region 120 may facilitate insertion of the femoral hip implant 100, or otherwise associating the femoral hip implant 100 with, the bony anatomy. For example, in some embodiments, the elongated insertion region 120 may be at least partially inserted into a prepared or natural intramedullary canal of the bony anatomy.

In various embodiments as described herein, the femoral hip implant 100 includes one or more features, geometries, and/or dimensions to optimize (e.g., maximize) fit within a greater population of patients. In addition, the femoral hip implant 100 includes one or more features arranged and configured to ensure improved short-term and long-term fixation with the intramedullary canal of the patient's femur. Moreover, in some embodiments, the femoral hip implant 100 may include one or more features, geometries, and/or dimensions to facilitate a direct anterior surgical approach. In use, an anterior approach is often preferred by various surgeons since it provides the most direct access to the anterior aspects of the patient's hip. In any event, in use, the femoral hip implant 100 is arranged and configured to optimize (e.g., maximize) fit within a greater population of patients regardless of the surgical approach being utilized (e.g., the implant is agnostic relative to surgical approach being used).

Referring to FIGS. 1A-1C, the femoral hip implant 100 includes an upper portion or shoulder 130 and a distal tip or end 132. As illustrated, the upper portion or shoulder 130 may be flat, or define a substantially flat surface. With additional reference to FIGS. 3 and 4, the femoral hip implant 100 may include a superior-inferior length L, as measured from the distal tip or end 132 to a resection level or plane Rp. For example, in some embodiments, it envisioned that a kit of femoral hip implants may be provided.

In some embodiments, the kit may contain a total of 13 femoral hip implants having various features including variable lengths L ranging between 93 mm and 117 mm, although this is but one configuration and it should be appreciated that the kit may have more or less number of implants and with implant having longer and/or shorter lengths.

Figure 6A:
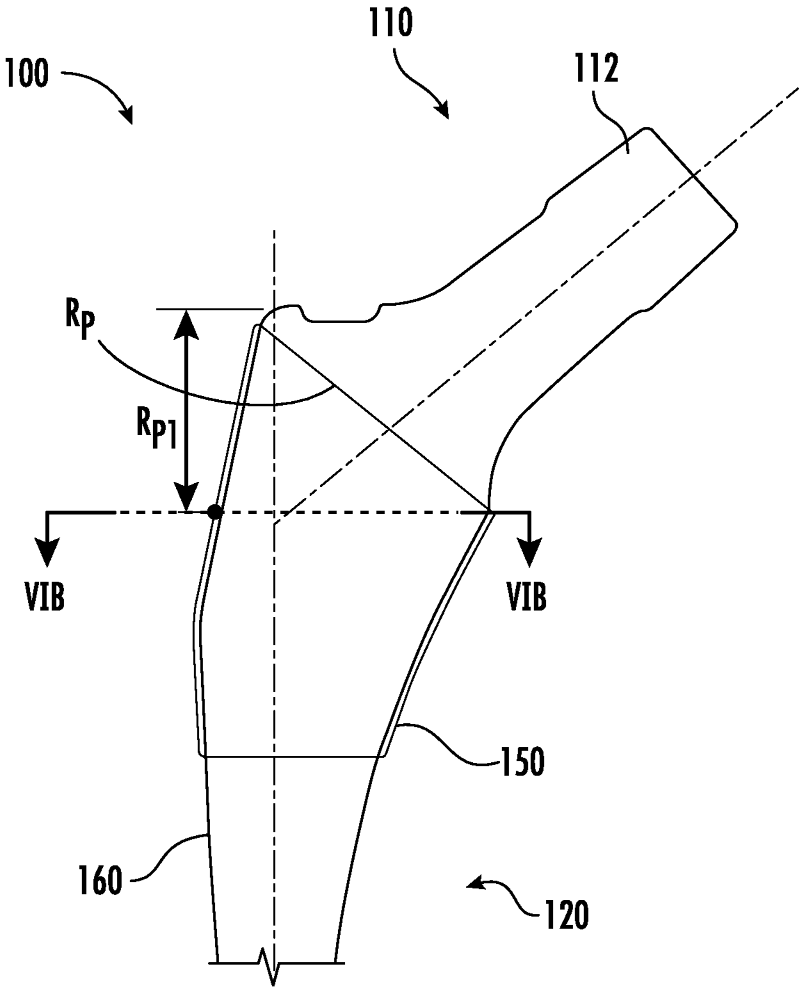
FIG. 6A illustrates a front (anterior) view of the femoral hip stem implant shown in FIG. 1A.

In various embodiments, the resection plane Rp may be positioned a distance of between 18 mm and 23 mm away from the shoulder 130 (e.g., intersection of the resection plane Rp with the medial side or surface 150 of the implant 100 illustrated by Rp1 in FIG. 6A), although this is but one configuration and other dimensions are envisioned. In use, as will be readily appreciated by one of ordinary skill in the art, the resection plane Rp roughly corresponds to an osteotomy point or plane where the proximal femur resection plane intersects the medial surface or side 150 when the femoral hip implant 100 is implanted within the intramedullary canal of the patient's femur.

In some embodiments, the neck 112 may have an angle α as measured between a central longitudinal axis of the elongated insertion region or stem 120 and a central longitudinal axis of the neck 112. In some embodiment, angle α may be approximately 125 to 135 degrees. In one preferred embodiment, angle α may be 131 degrees, although other angles are envisioned.

In use, the neck 112 may be provided in a standard configuration and a high offset configuration. In various embodiments, the neck 112, in the standard configuration, may include a neck offset No between 32 mm and 44 mm, a neck length $N_L$ between 27.9 mm and 35.5 mm, and a neck height $N_H$ between 26 mm and 33 mm. In various embodiments, the neck 112, in the high offset configuration, may include a neck offset No between 38 mm and 52 mm, a neck length $N_L$ between 31.7 mm and 40.5 mm, and a neck height $N_H$ between 26 mm and 33 mm. Although these are just a few of the available configurations and other dimensions are envisioned.

With continued reference to the FIGS., the femoral hip implant 100 also includes a medial surface or side 150, a lateral surface or side 160, an anterior surface or side 170, and a posterior surface or side 180.

Figure 5:
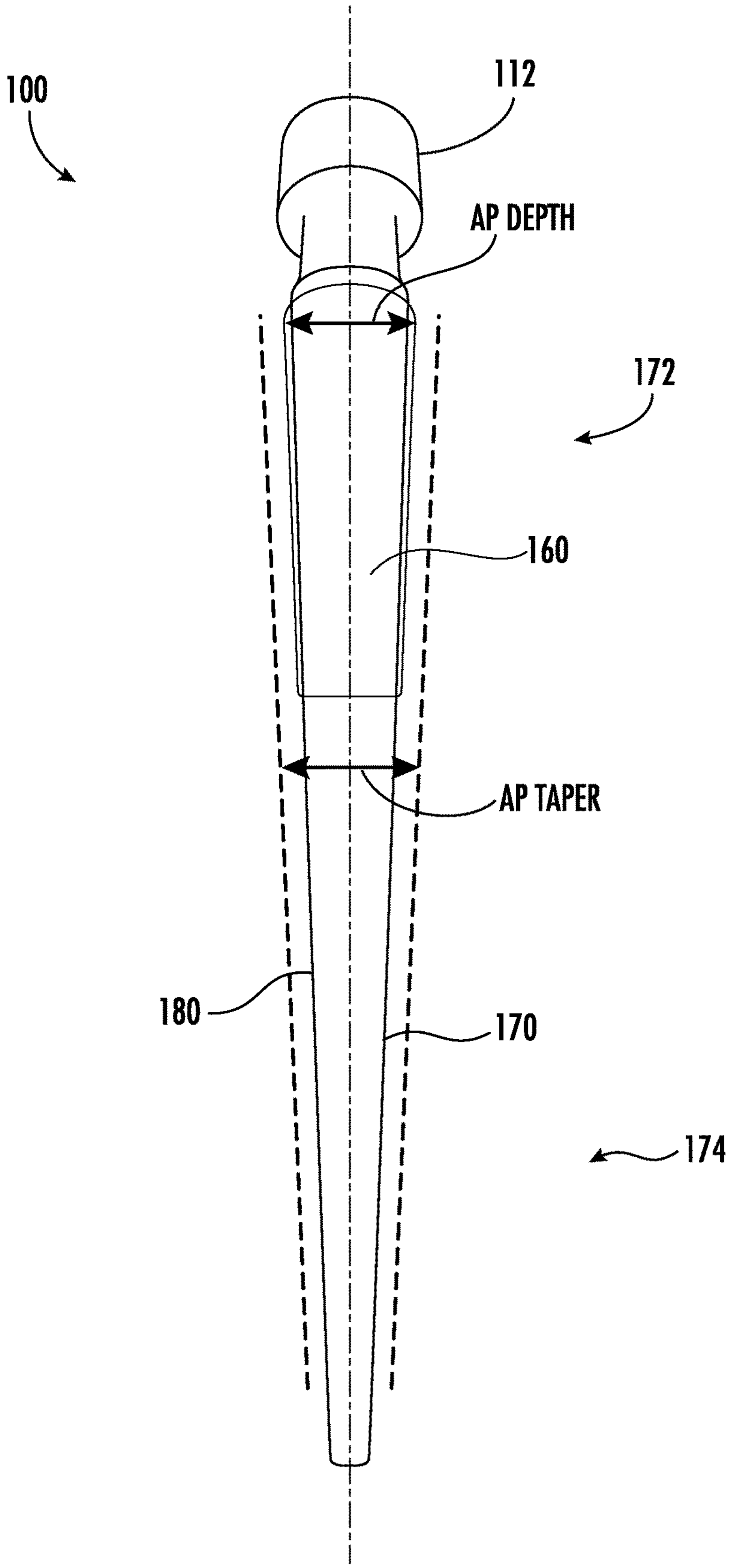
FIG. 5 illustrates a side (lateral) view of the femoral hip stem implant shown in FIG. 1A.
Figure 6B:
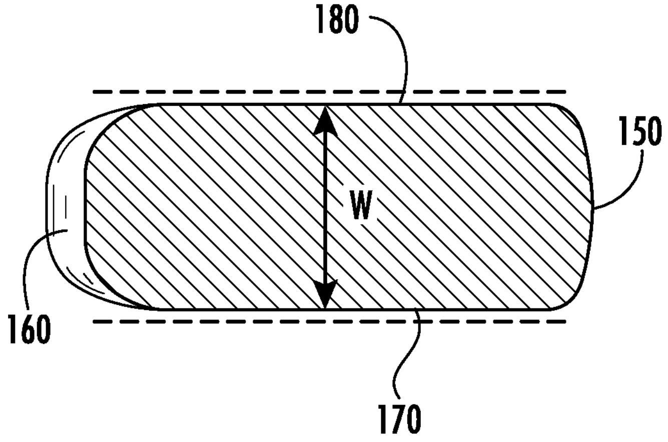
FIG. 6B illustrates a cross-sectional view of the femoral hip stem implant shown in FIG. 6A, the cross-sectional view taken along line VIB-VIB.

With reference to FIGS. 5-6B, the shoulder 130 may have a width W (e.g., maximum width of the femoral hip implant 100), as measured between the anterior surface or side 170 and the posterior surface or side 180 of between 12 mm and 24.0 mm, although this is but one configuration and other dimensions are envisioned. In addition, with reference to FIGS. 1B and 5, the cross-sectional area may include an AP Taper of between 1.0 degree and 10.0 degrees, although this is but one configuration and other dimensions are envisioned.

Figure 3:
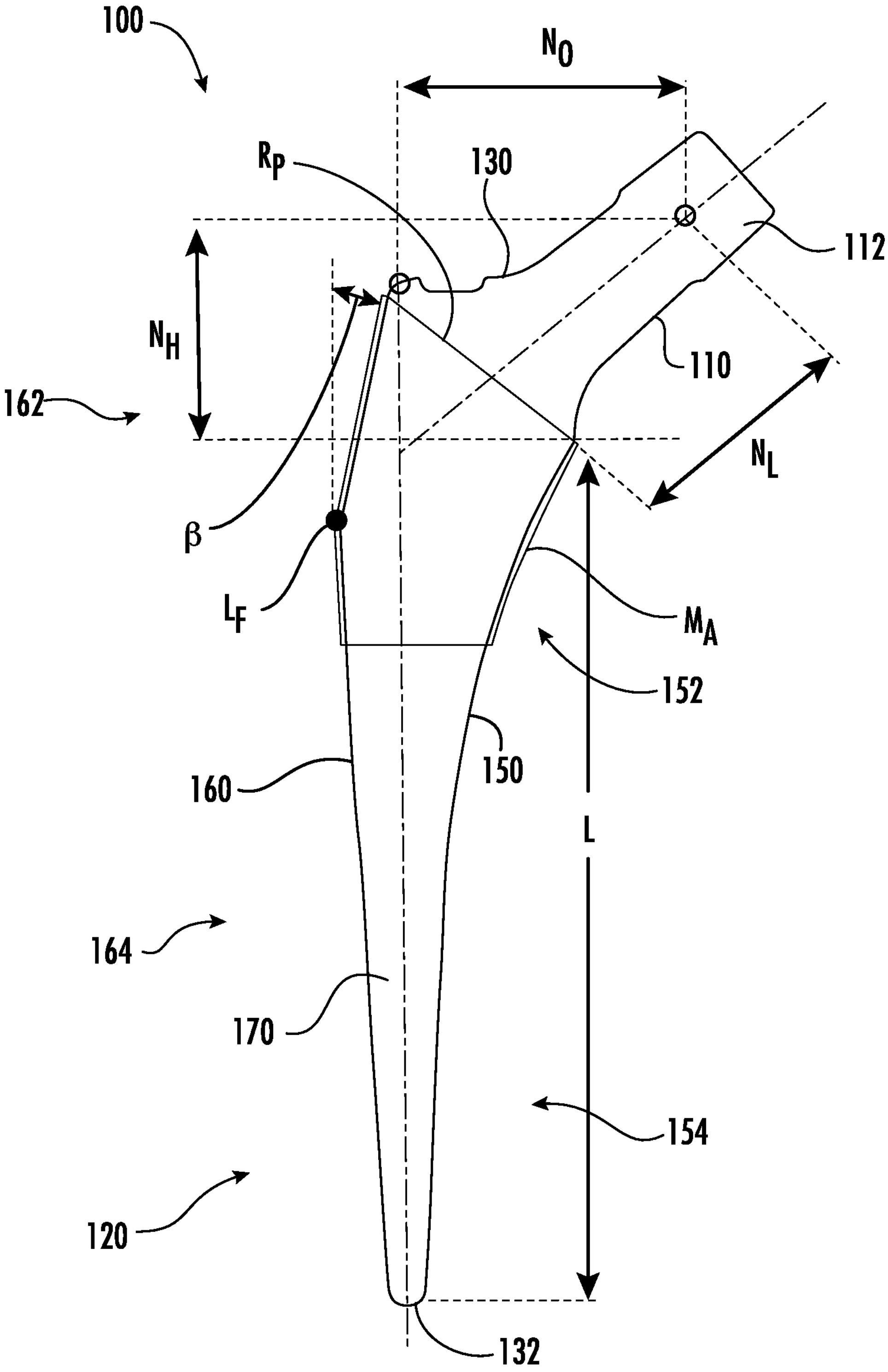
FIG. 3 illustrates an alternate frontal (anterior) view of the femoral hip stem implant shown in FIG. 1A.
Figure 4:
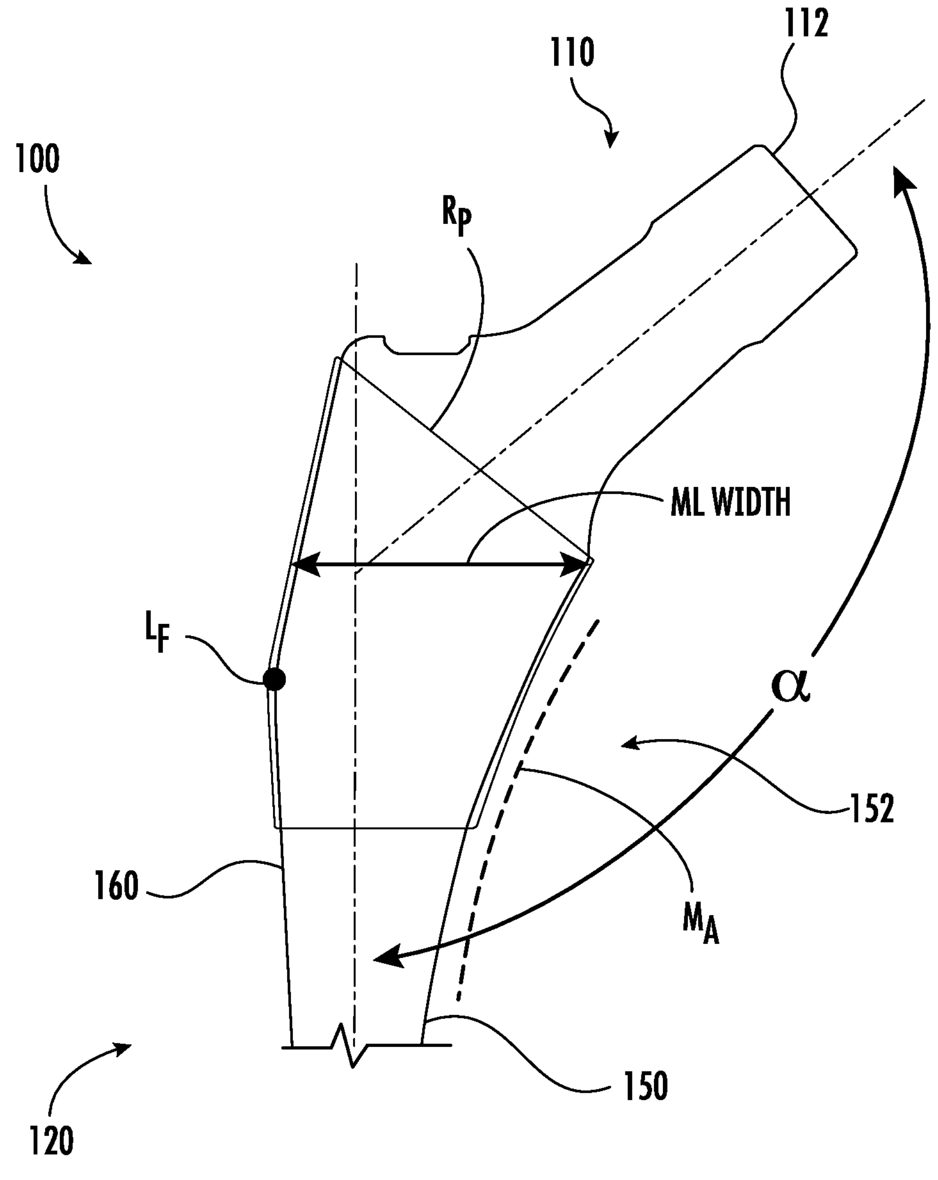
FIG. 4 illustrates an alternate frontal (anterior) view of the femoral hip stem implant shown in FIG. 1A.

As illustrated, in some embodiments, the lateral surface or side 160 includes a proximal region 162 and a distal region 164. The lateral surface or side 160 in the proximal region 162 extending distally from a lateral end portion of the upper portion or shoulder 130 to the proximal end of the distal region 164. As illustrated, the lateral surface or side 160 may taper away from the medial surface or side 150 in the proximal region 162. Meanwhile, in the distal region 164, the lateral surface or side 160 may taper towards the medial surface or side 150. Thus arranged, the lateral surface or side 160 may define an apex or a lateral flare $L_F$. With reference to FIGS. 3 and 4, the proximal region 162 of the lateral surface or side 160 may define a flare angle R between 9 and 12 degrees. The apex or lateral flare $L_F$ may be positioned a horizontal distance of between 8.3 mm and 13.7 mm away from the lateral end of the shoulder 130 and a vertical distance of between 12 mm and 24 mm away from the resection plane Rp, although these are but one configuration and other dimensions are envisioned. In use, the apex or lateral flare $L_F$ may be positioned a variable distance between sequentially sized implants. For example, in some embodiments, as the length of the femoral hip implant increases, the distance between the lateral end of the shoulder 130 and the apex or flare $L_F$ may increase non-proportionally. For example, the distance between one set of sequentially sized implants within the kit may increase by 0.4 mm while the distance between other sets of sequentially sized implants within the kit may increase by 0.5 mm or 0.8 mm, although these are but one configuration and other dimensions are envisioned.

The medial surface or side 150 may also include a proximal region 152 and a distal region 154. In use, the proximal region 152 may generally correspond to the metaphysis and the distal region 154 may generally correspond to the diaphysis when the femoral hip implant 100 is implanted into the patient's femur's intramedullary canal.

As illustrated, the proximal region 152 of the medial surface or side 150 may include a medial arc or curvature $M_A$. As illustrated, in various embodiments, the medial arc or curvature $M_A$ may be a constant radius of curvature, although this is not necessary. The distal region 154 of the medial surface or side 150 may taper towards the lateral surface or side 160. Thus arranged, the elongated insertion region or stem 120 of the femoral hip implant 100 may include a maximum medial-lateral size or width ("ML Width") between the medial surface or side 150 and the lateral surface or side 160 at the resection plane Rp (FIG. 4). In use, the ML Width may be sized a variable distance between sequentially sized implants. For example, in some embodiments, as the length of the femoral hip implant increases, the ML width may increase non-proportionally. For example, the ML width between one set of sequentially sized implants within the kit may increase by 1.0 mm while the ML Width between other sequentially sized implants within the kit may increase by 0.8 mm, 0.9 mm, 1.2 mm, etc. Although this is but one configuration and other dimensions are envisioned.

Referring to FIGS. 1B and 5, the elongated insertion region or stem 120 of the femoral hip implant 100 may include an anterior-posterior proximal region 172 and an anterior-posterior distal region 174. As illustrated, the elongated insertion region or stem 120 may include a maximum anterior-posterior size or depth ("AP Depth") between the anterior surface or side 170 and the posterior surface or side 180. In addition, the femoral hip implant 100 may include an anterior-posterior taper ("AP Taper"). Thus arranged, in some embodiments, as generally illustrated, the elongated insertion region or stem 120 may include tapers in both the anterior-posterior widths as well as the medial-lateral widths. In other embodiments, elongated insertion region or stem does not taper in one or both of the anterior-posterior and medial-lateral widths.

As illustrated, the anterior-posterior distal region 174 may include an AP Taper. In some embodiments, in accordance with one or more features of the present disclosure and contrary to conventionally known prior art femoral hip implants, as the length of the femoral hip implant increases, the AP Taper decreases. As such, larger length femoral hip implants 100 in accordance with the present disclosure have a shallower profile. Alternatively, in some embodiments, the AP Taper may increase as the length of the femoral hip implant increases. However, in accordance with one or more features of the present disclosure and contrary to conventionally known prior art femoral hip implants, the AP Taper may not increase sequentially as the length of the femoral hip implant increases. That is, as the length of the femoral hip implant increases, the AP Taper may increase non-proportionally. For example, in some embodiments, the femoral hip implant may have an AP Taper of between 3.5 degrees to 6.5 degrees. However, as the length of the implant increases, the AP Taper between one set of sequentially sized implants within the kit may increase by 0.15 degree, while the AP Taper between other sequentially sized implants within the kit may increase by 0.20 degrees or 0.25 degrees. Although these are just a few of the available configurations and other dimensions are envisioned.

Figure 7:
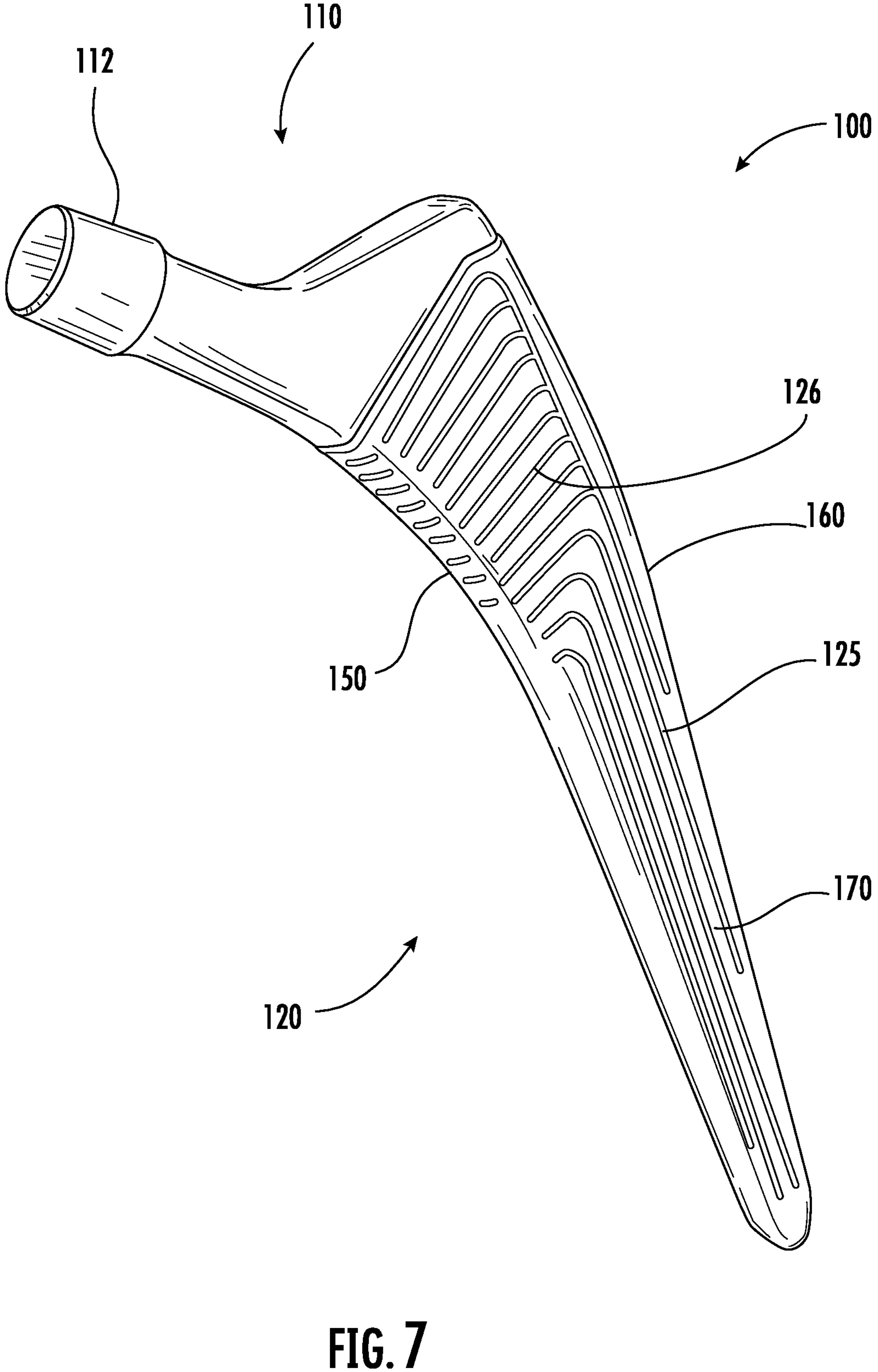
FIG. 7 illustrates a perspective view of an alternate embodiment of a femoral hip stem implant in accordance with one or more features of the present disclosure, the implant illustrated with a porous coated surface and macro-grooves for enhanced bone-ingrowth.
Figure 8A:
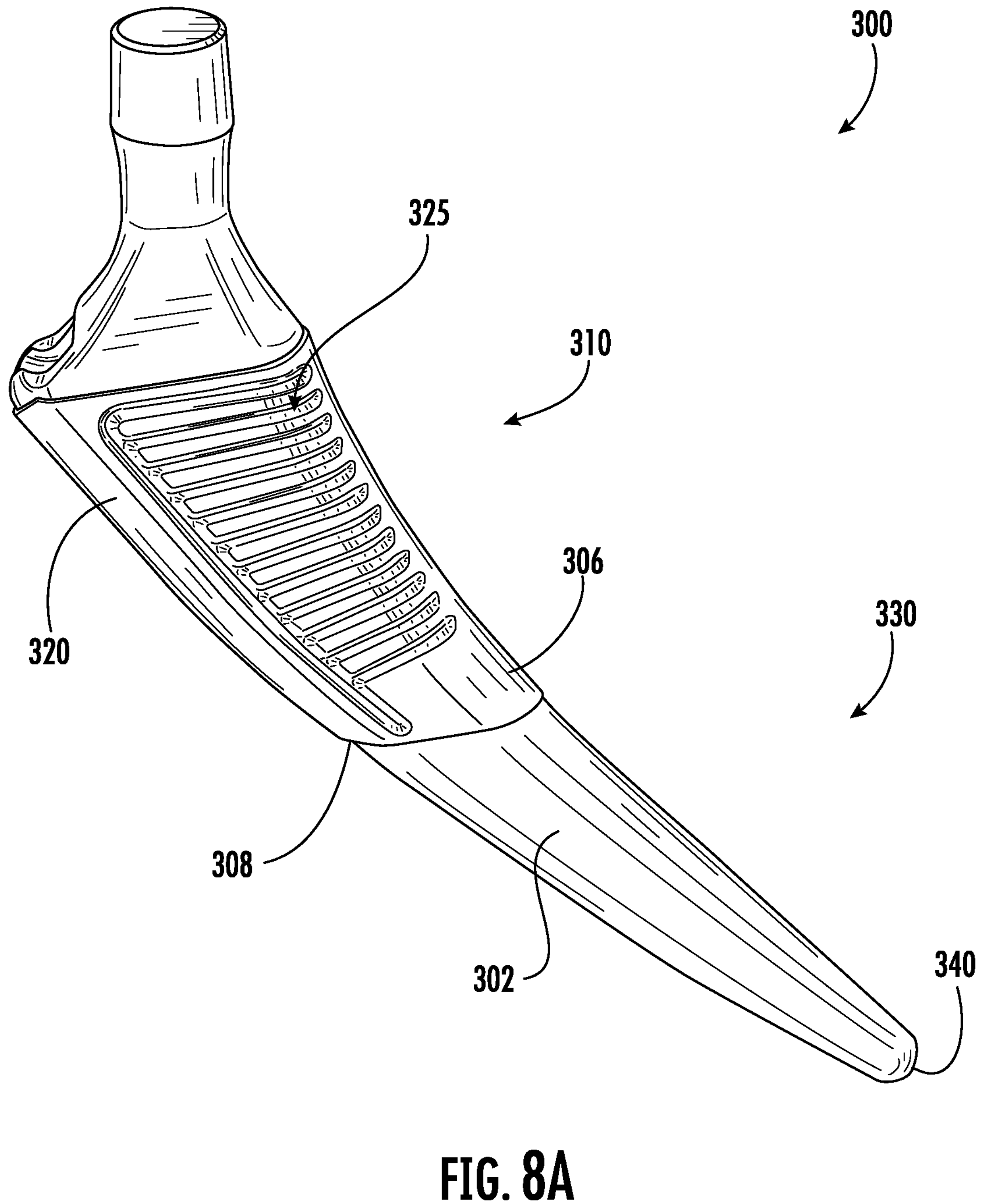
FIGS. 8A-8E illustrate various views of an alternate embodiment of a femoral hip stem implant in accordance with one or more features, geometries, and/or dimensions of the present disclosure, FIGS. 8A-8D illustrating a collarless version of the femoral hip stem implant, FIG. 8E illustrating a collar version of the femoral hip stem implant.
Figure 8B:
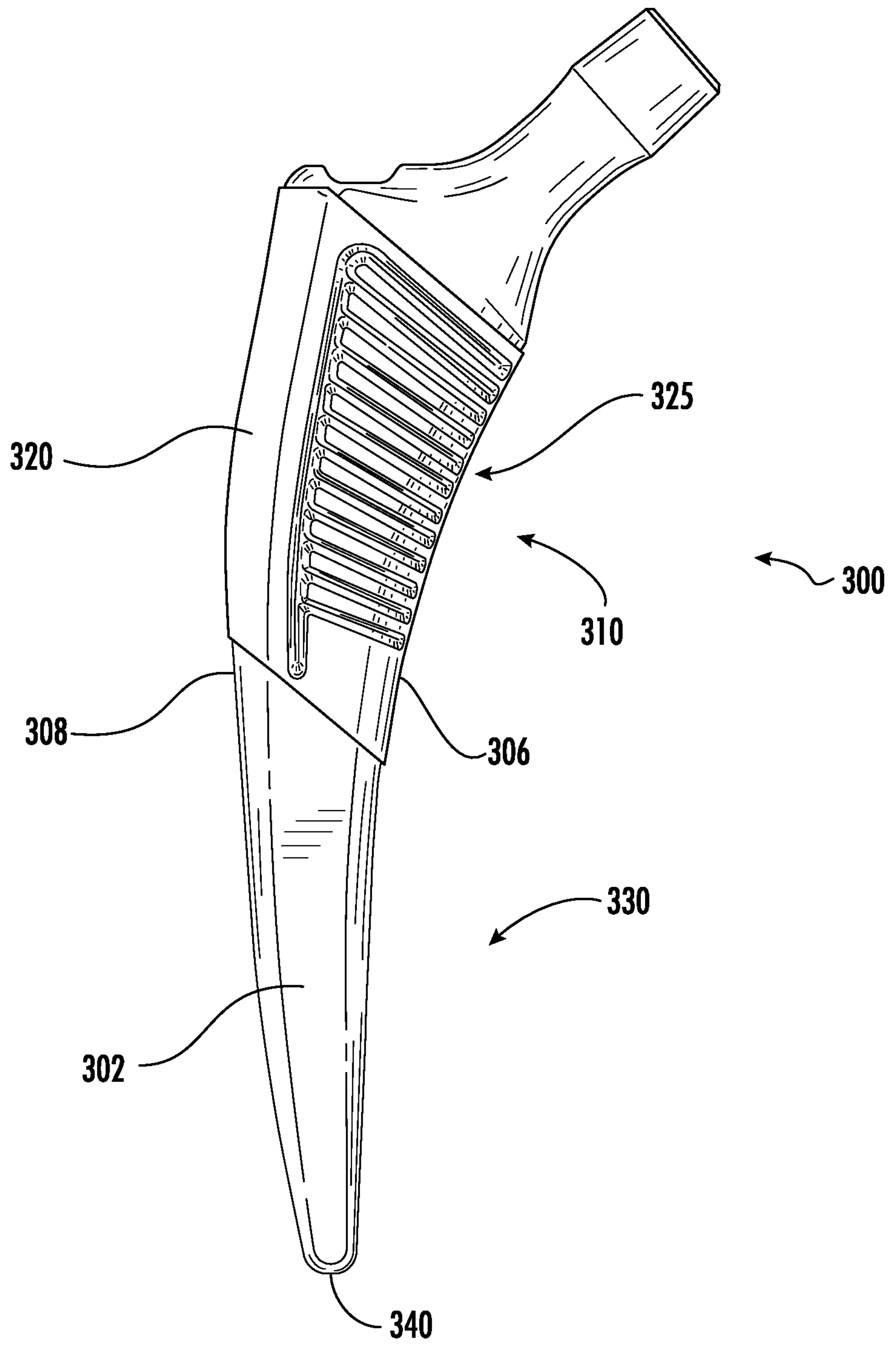
Figure 8C:
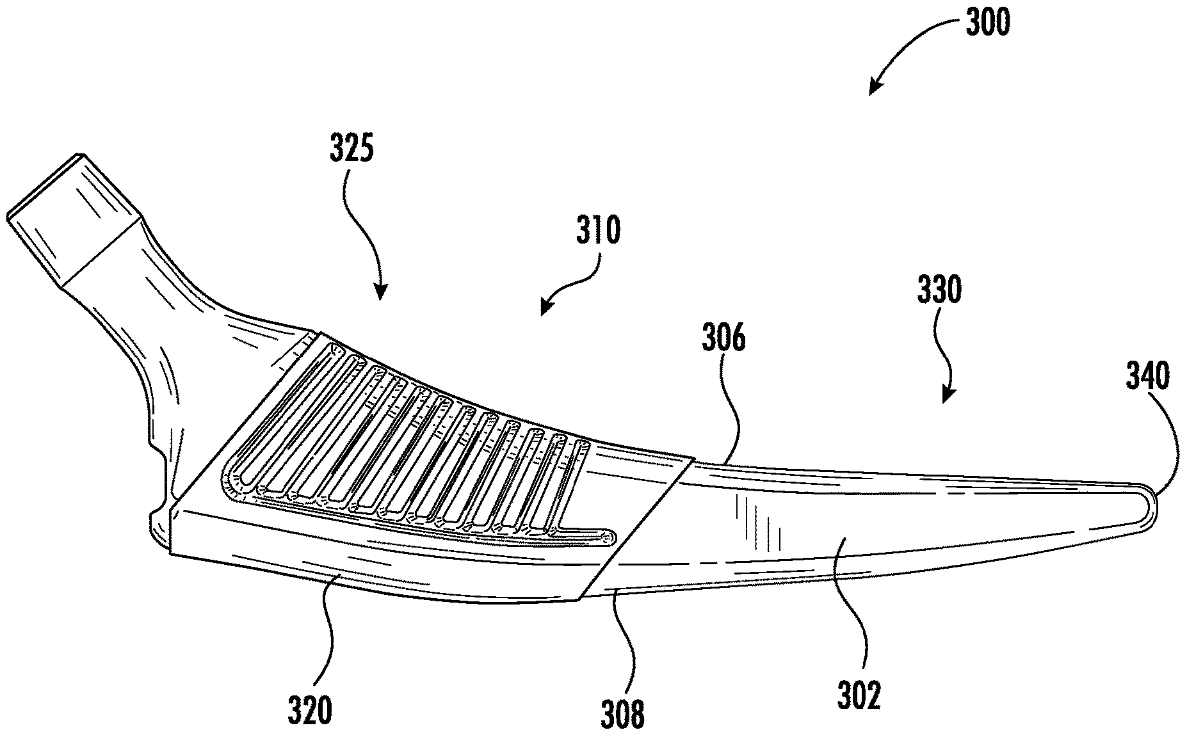
Figure 8D:
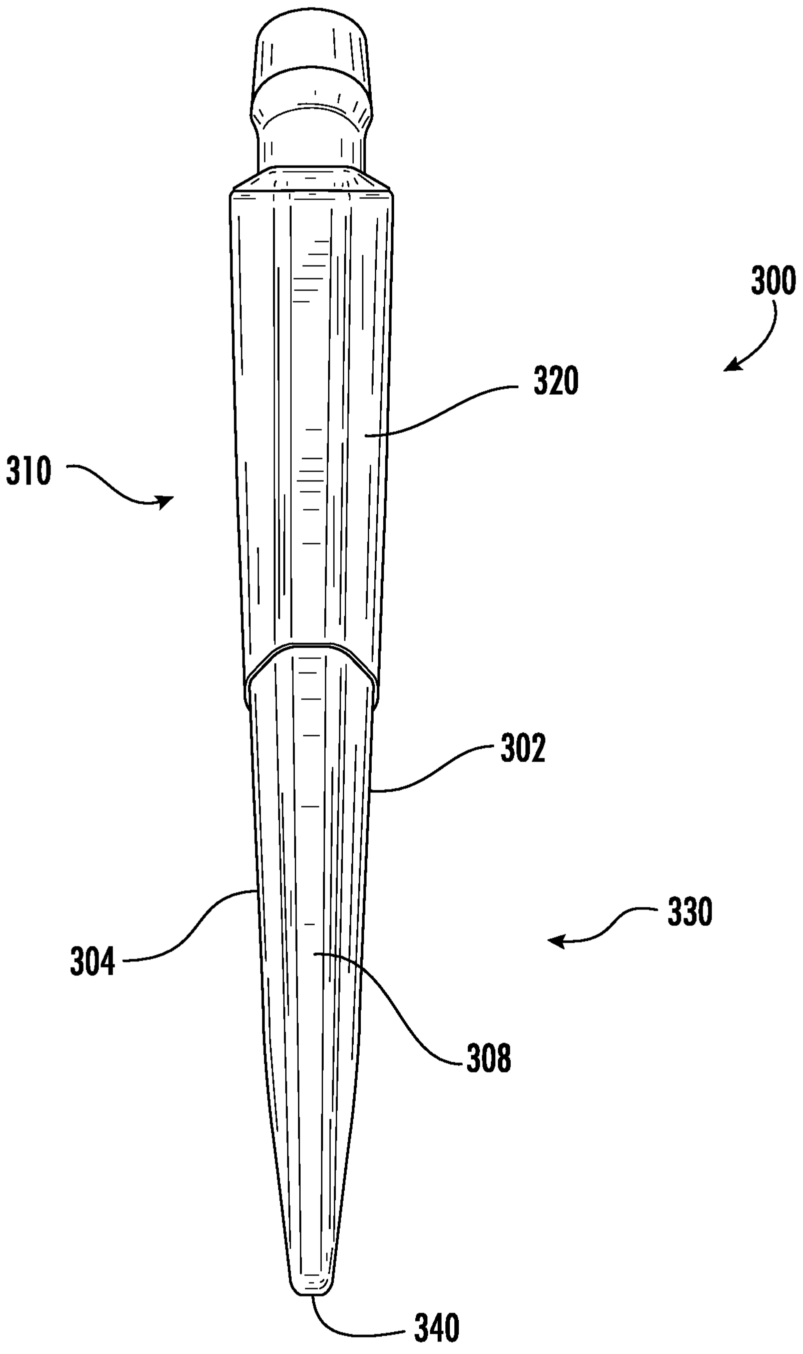
Figure 8E:
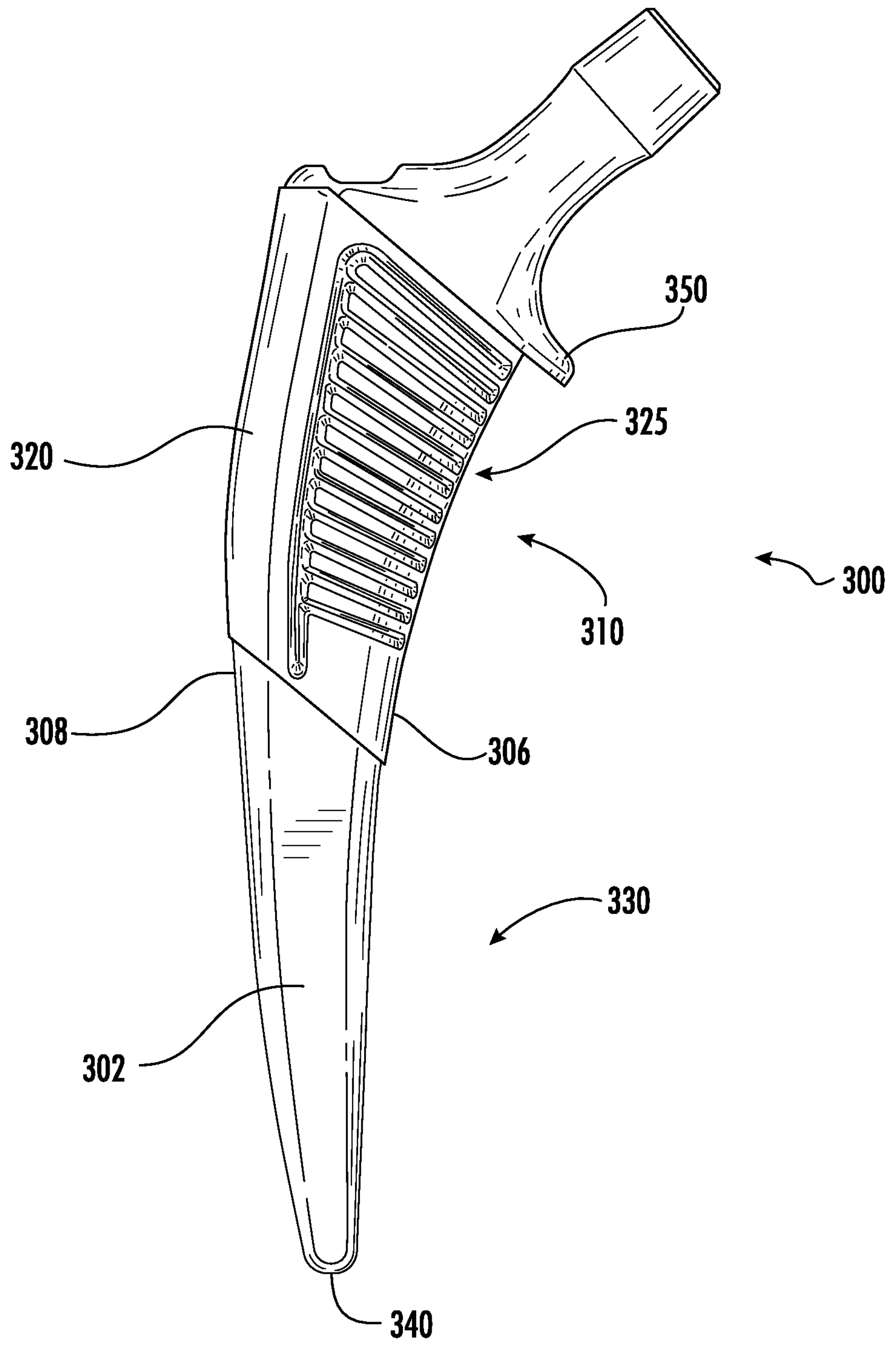

In various embodiments, the femoral hip implant 100 may include a porous coating and/or roughened surface 125 (FIG. 7) (terms used interchangeably herein) applied thereto for additional boney in-growth and/or fixation. In some embodiments, the porous coating 125 may be printed, sprayed, or sintered onto the bone facing surfaces of the femoral hip implant 100. For example, the porous coating 125 may be formed by plasma spraying titanium, cobalt chrome, zirconium, oxidized zirconium, or stainless steel over the bone facing surfaces of the femoral hip implant. Alternatively, the porous coating 125 could be a hydroxyapatite or other similar coating known in the art to enhance bony-ingrowth. In some embodiments, the entire femoral hip stem implant could be coated. Alternatively, only sections of the implant may be coated as will be described in greater detail below. In addition, and/or alternatively, the femoral implant 100 may include one or more roughened surfaces to facilitate enhanced bony-ingrowth. For example, referring to FIG. 7, the femoral hip stem implant 100, or at least portions thereof, may include one or more macro-grooves 126. As illustrated, the grooves 126 may be formed within the anterior and posterior surfaces or sides 170, 180 of the implant 100.

With reference to FIGS. 8A-11, an alternate embodiment of an orthopedic femoral hip implant 300 is disclosed. As illustrated, the femoral hip implant 300 includes a proximal region 310 and a distal region 330. In addition, the femoral hip implant 300 includes an anterior surface or side 302 (terms used interchangeably herein without the intent to limit or distinguish), a posterior side 304 opposite the anterior side 302, a medial side 306, and a lateral side 308. In various embodiments, the proximal region 310 includes a porous coated and/or roughened surface or region 320 such as, for example, a titanium plasma-sprayed porous coating, although any suitable porous coating now known or hereafter developed can be used including those previously described herein.

In addition, within the porous coated region 320, the anterior and posterior sides 302, 304 of the implant 300 include grooves 325 formed therein to facilitate improved engagement with the remaining patient's bone. As illustrated, in some embodiments, the grooves 325 are angled downwards from the lateral side 308 toward the medial side 306, although it is envisioned that the grooves may be angled upwards (e.g., grooves 325 formed on the anterior and posterior sides 302, 304 are angled relative to a central longitudinal axis of the implant 300). In some embodiments, in accordance with one or more features of the present disclosure, the grooves 325 may extend to, and along, at least a portion of the medial side 306 of the femoral hip implant 300. That is, as illustrated in FIGS. 8A-8E, the grooves 325 wrap around a corner of the implant 300 (e.g., the grooves 325 may wrap around the medial blend radius of the implant 300 from the anterior-posterior aspect or region to the medial aspect or region of the stem). For example, the grooves 325 wrap around the corner formed by the anterior side 302 and the medial side 306. Thus arranged, by wrapping or extending the grooves 325 from the anterior side 302 to the medial side 306, improved engagement with cortical bone has been discovered (e.g., grooves 325 react better with patient's remaining bone at the conclusion of the broaching process thereby leading to improved long-term stability).

Figure 9:
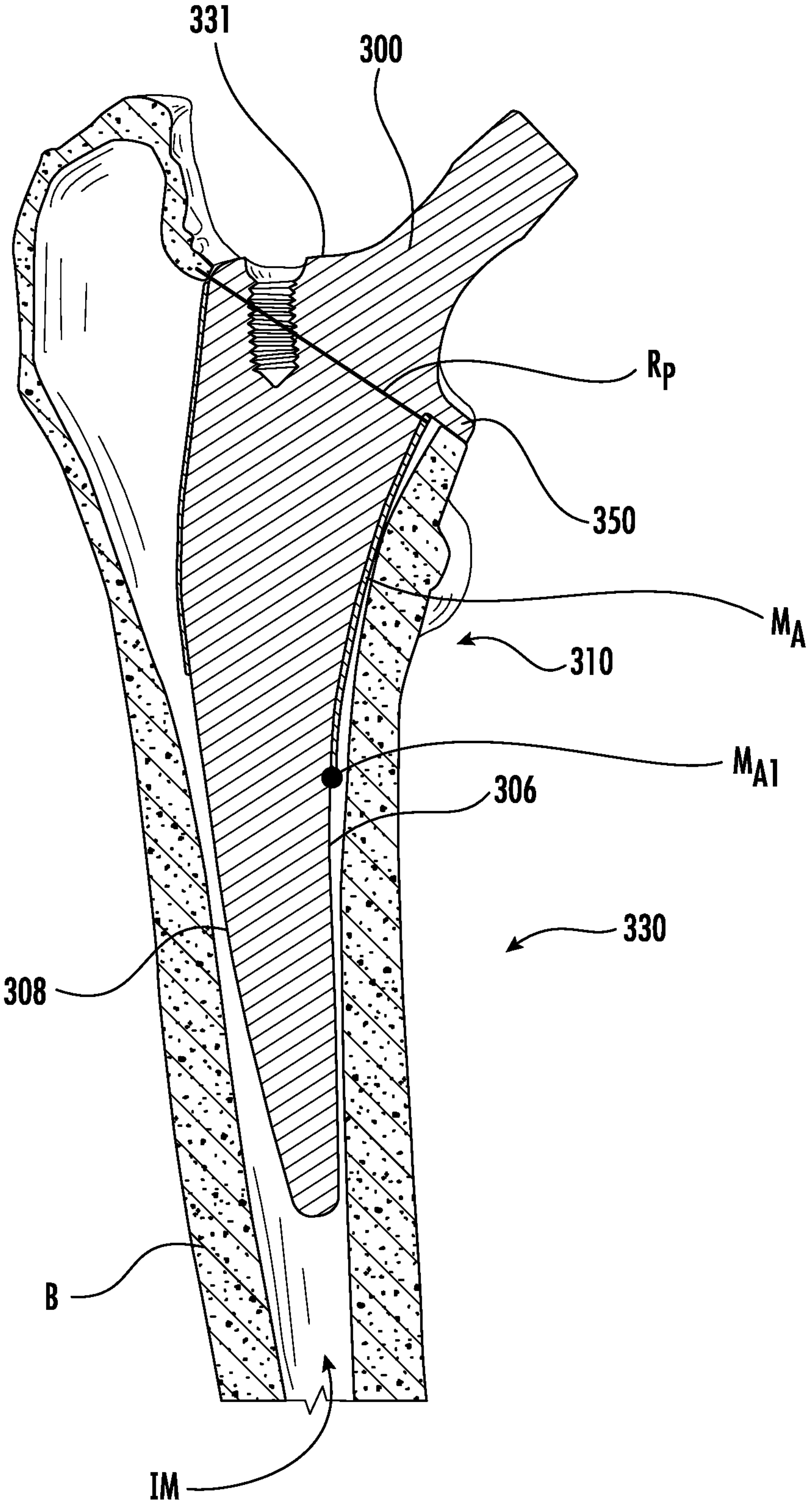
FIG. 9 illustrates a medial-lateral cross-sectional view of the femoral hip stem implant of FIGS. 8A-8E implanted with an intramedullary canal of a patient's bone.

In addition, with reference to FIG. 9 and as previously mentioned, in some embodiments, the medial side 306 of the implant 300, at least within the proximal region 310, includes a constant radius or arc of curvature $M_A$. That is, with additional reference to FIG. 11 and as will be readily appreciated by one of ordinary skill the art, the implant 300 may be said to have a resection plane Rp, a mid-body plane MBp, and a three-quarter distal plane Dp. In a preferred embodiment, the medial side 306 of the proximal region 310 of the implant 300 includes a constant arc of curvature $M_A$. Thus arranged, in use, the implant 300 is configured to provide an improved press-fit with the patient's bone remaining from the broaching process. In addition, when combined with the wrapping of the grooves 325 from the anterior side 302 to the medial side 306, improved on-growth along the medial arc has been discovered. In use, grooves 325 may improve resistance to femoral stem subsidence in the short term and provide potential for additional axial support. Long term boney ingrowth may improve axial stability by providing a number of steps intended to support the stem. In some embodiments, with reference to FIG. 9, the constant arc of curvature $M_A$ extends from the resection plane Rp to transition point $M_{A1}$. In some embodiment, the constant arc of curvature $M_A$ may be between 100 mm to 150 mm, although this is but one configuration and other dimensions are envisioned. In some embodiments, the transition point Mai may be a distance of 35 percent to 40 percent of the overall stem length as measured from the shoulder 331 to the distal tip 340.

Figure 12A:
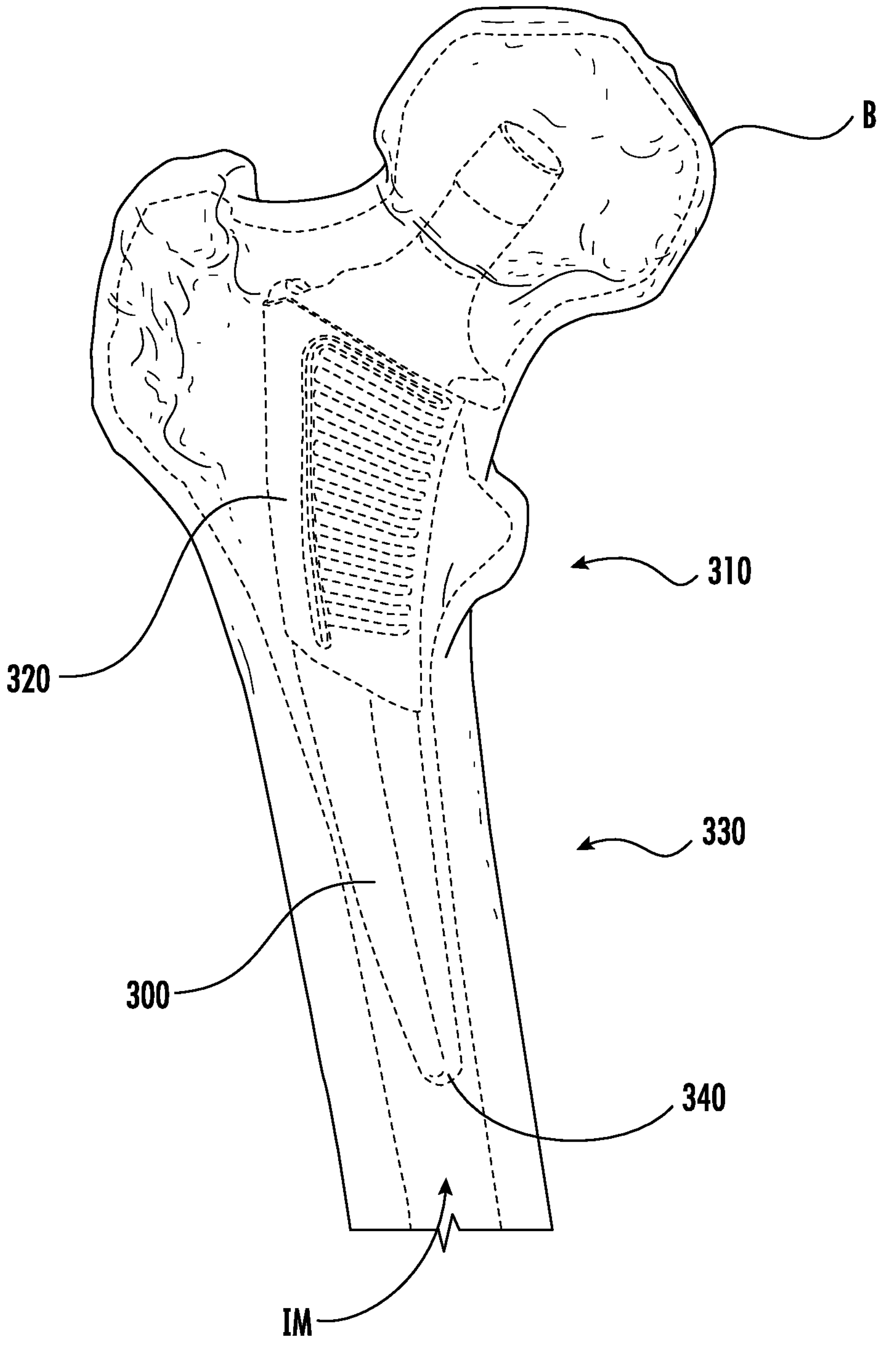
FIGS. 12A-12F illustrate the fit of the femoral hip stem implant of FIGS. 8A-8E implanted with an intramedullary canal of a patient's bone along various cross-sectional areas in accordance with one or more features of the present disclosure.
Figure 12B:
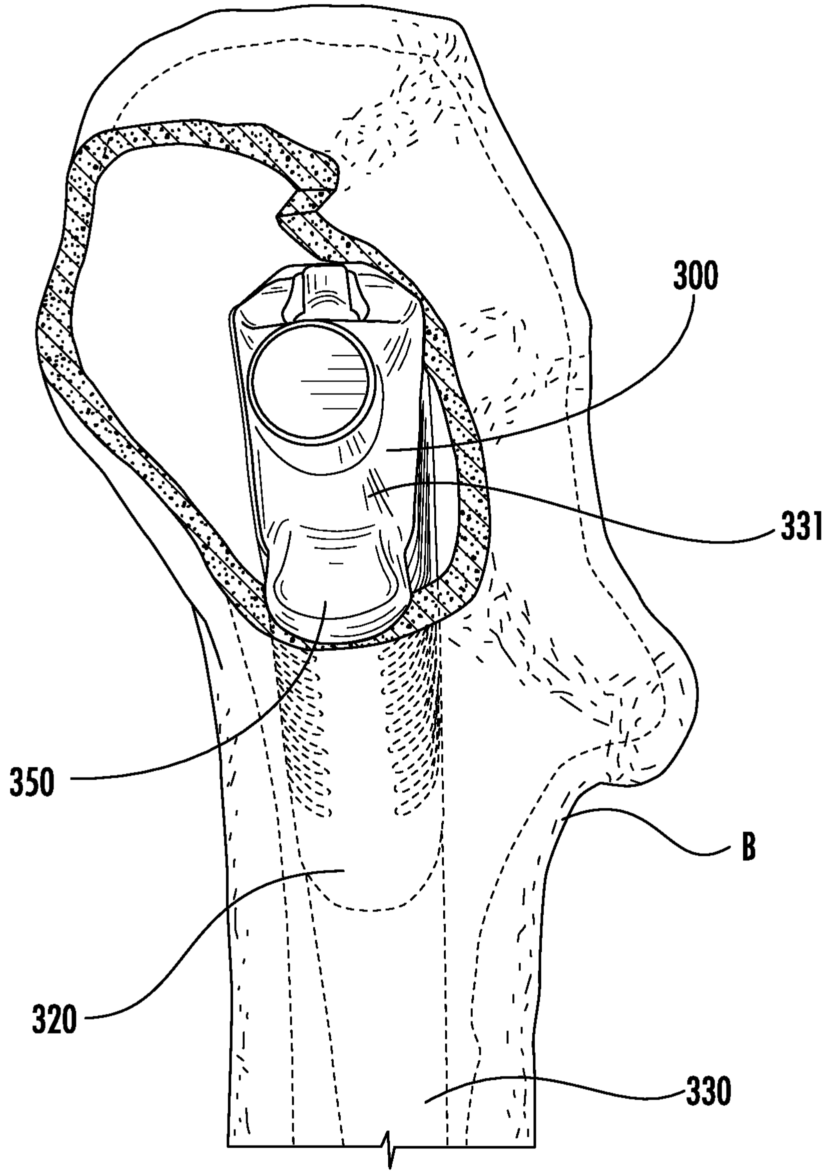
Figure 12C:
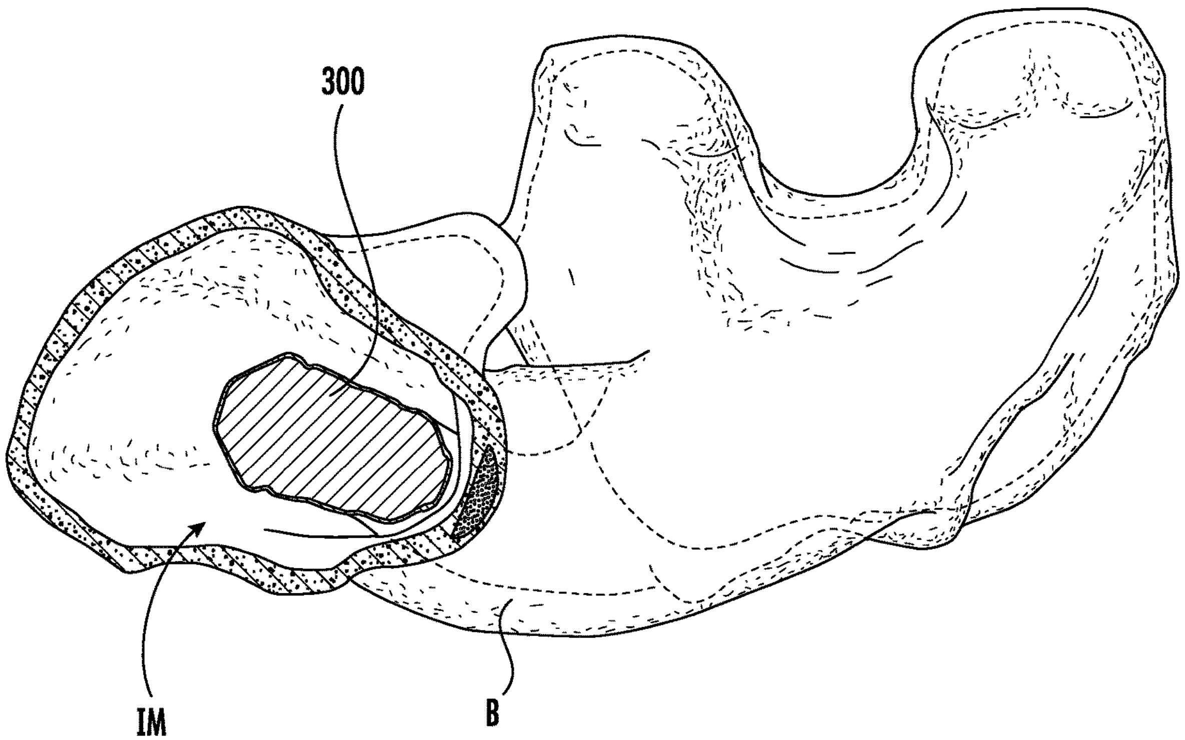
Figure 12D:
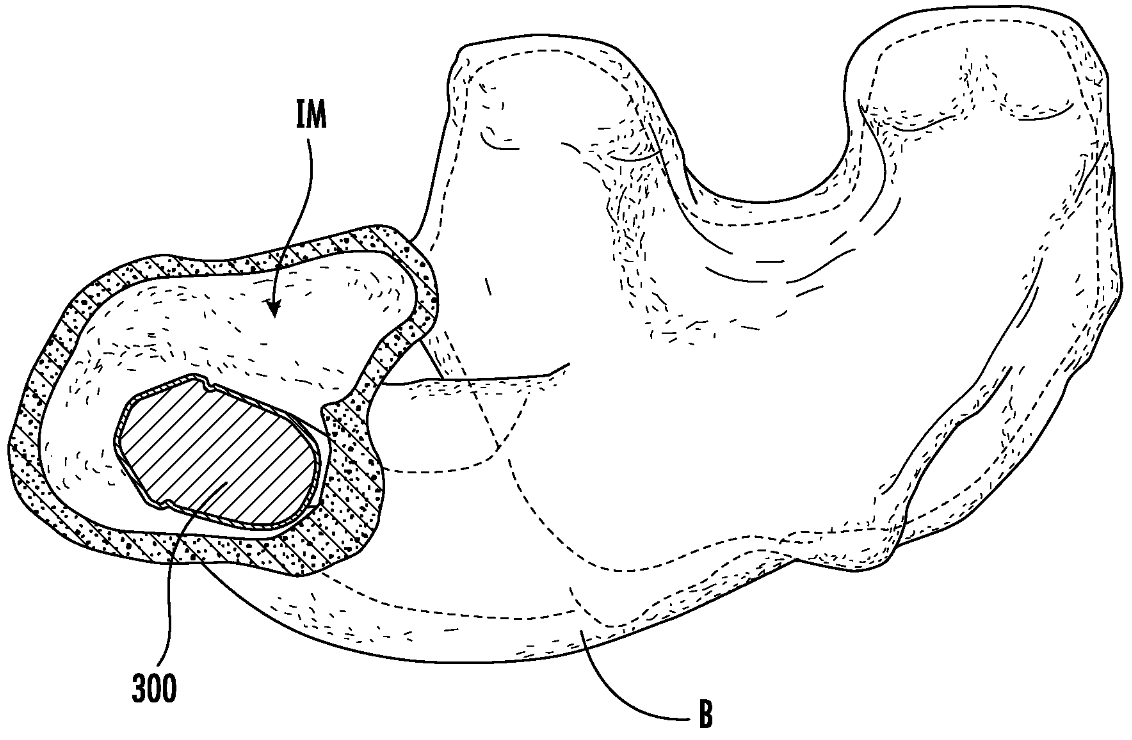
Figure 12E:
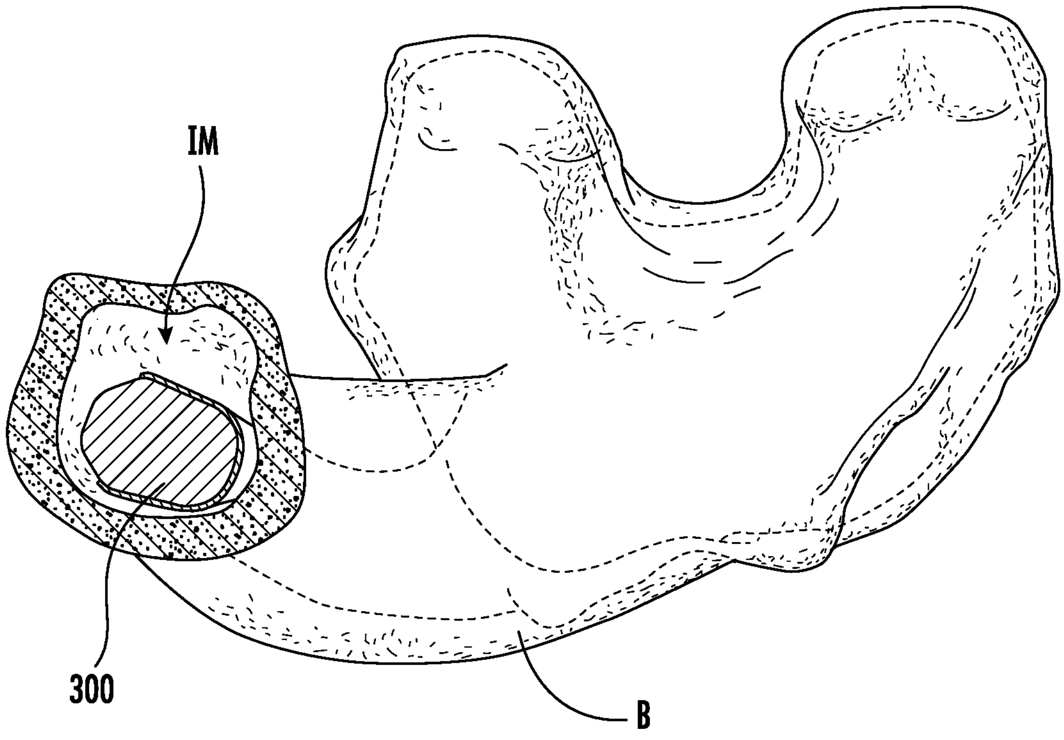
Figure 12F:
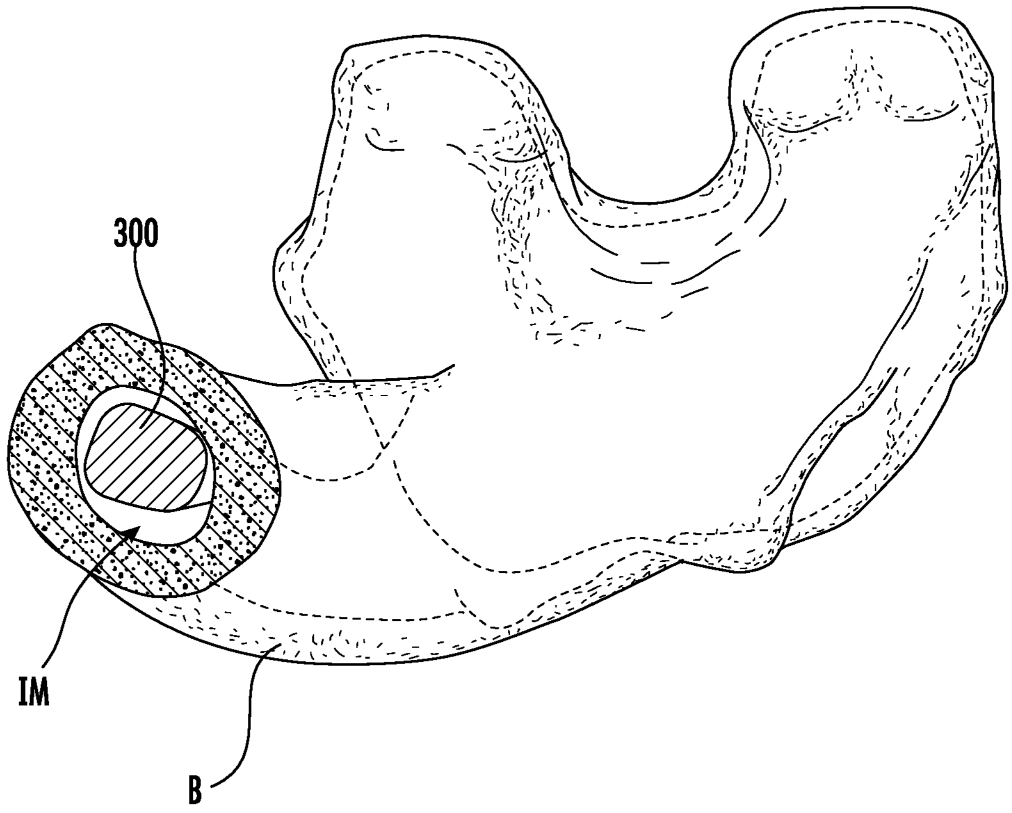

In addition, in some embodiments, the implant 300 is optimized so that, in use, when positioned within the intramedullary canal IM of the patient's bone B, a portion of the lateral side 308 of the implant 300 positioned beneath the patient's lesser trochanter is arranged and configured to provide a press-fit with the patient's bone remaining from the broaching process (FIGS. 12A and 12B).

Figure 10:
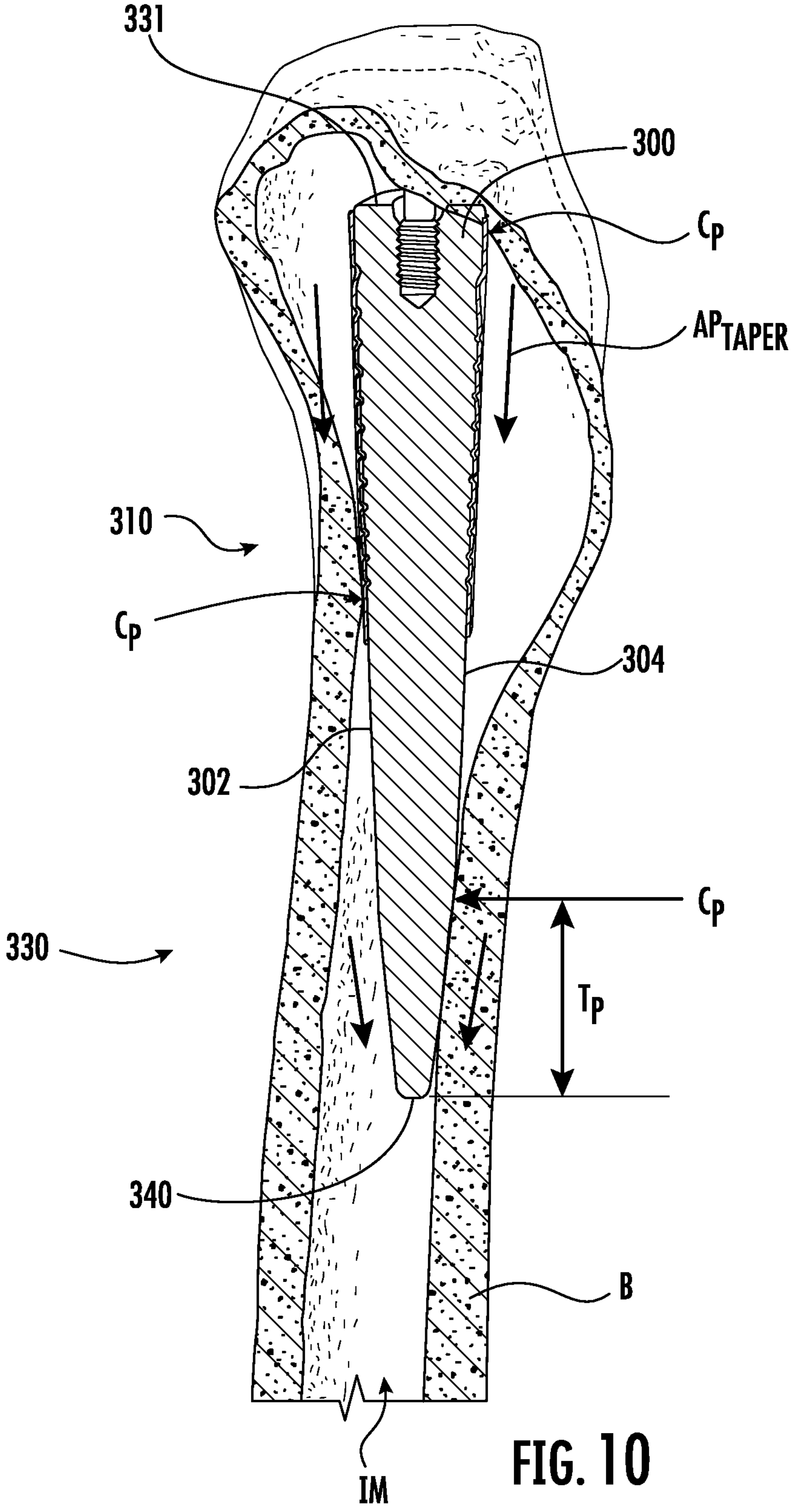
FIG. 10 illustrates an anterior-posterior cross-sectional view of the femoral hip stem implant of FIGS. 8A-8E implanted with an intramedullary canal of a patient's bone.
Figure 11:
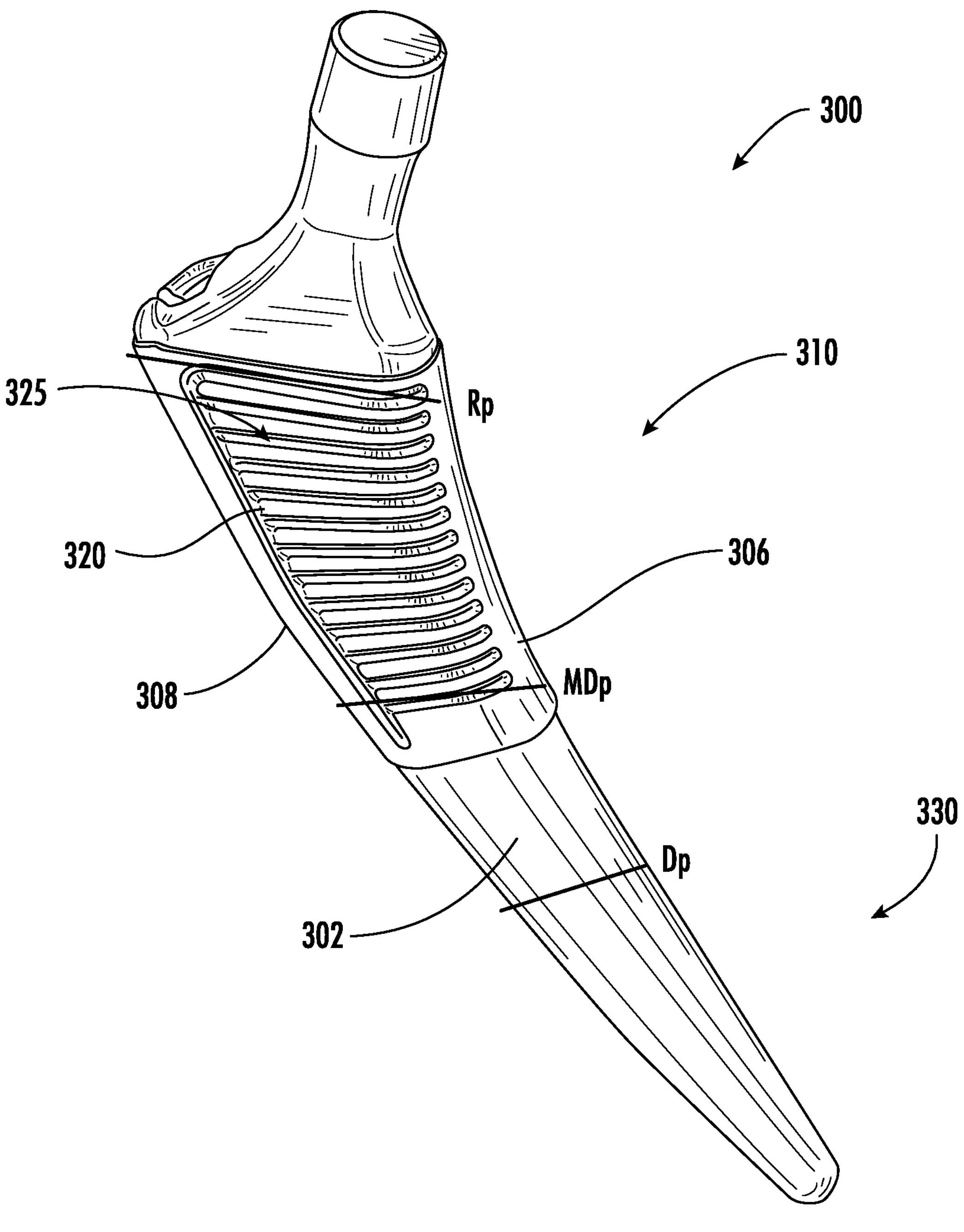
FIG. 11 illustrates an alternate perspective view of the femoral hip stem implant of FIGS. 8A-8E.

In addition, with reference to FIG. 10, in some embodiments, the implant 300 may include a dual-tapered AP Taper. That is, as previously mentioned, the implant 300 may include an AP Taper extending from the shoulder 331 towards the distal tip 340. As illustrated, in some embodiments, the implant 300 may incorporate a second AP Taper adjacent to, or proximate, the distal tip 340 in the distal region 330 of the implant 300 wherein the second AP Taper is different from the first AP Taper. That is, as illustrated in the embodiment of FIG. 10, the implant 300 may include first and second AP Tapers with the first AP Taper extending from the shoulder 331 towards the distal tip 340. The first AP Taper terminating at a transition point (Tp). Thereafter, the implant 300 may include a second, alternate AP Taper extending from the transition point (Tp) to the distal tip 340. That is, in some embodiments, the anterior side 302 and the posterior side 304 each taper inwards towards a central longitudinal axis of the implant 300 (e.g., anterior and posterior sides 302, 304 each taper towards each other as they progress towards the distal tip 340 of the implant 300). In some embodiments, as illustrated, the AP Taper is symmetrical (e.g., taper on the anterior side 302 is the same as the taper on the posterior side 304). In some embodiments, the AP Taper may be configured with an angle of approximately 3.5 degrees to 6.5 degrees. However, at a transition point (Tp), the AP Taper may transition or change. In one preferred embodiment, the AP Taper proximate the distal tip 340 may change by one-degree such that the AP Taper may be configured with an angle of approximately 4.5 degrees to 7.5 degrees. Although these are but one configuration and other dimensions are envisioned. In this arrangement, the AP Taper proximate the distal tip 340 gives the distal region 330 of the implant 300 a more pronounced V-shaped configuration. In addition, the distal tip 340 of the implant 300 is arranged and configured to avoid impingement of the distal tip with the patient's cortical bone during implantation as illustrated in FIG. 10. This will allow the stem to fully seat within the intramedullary canal and provide better fill of the intramedullary canal by avoiding early tip impingement. In some embodiments, the transition point (Tp) may be positioned at a point between 15 percent and 25 percent of the total length of the hip stem implant as measured from the shoulder 331 to the distal tip 340. In some embodiments, the transition point (Tp) may be positioned at a point positioned approximately 18 mm to 35 mm from the distal tip 340.

In addition, with continued reference to FIG. 10, by providing an AP Taper, the implant 300 is configured to provide point contact Cp with the patient's bone B remaining from the broaching process along the anterior and posterior sides 302, 304 thereof. For example, as illustrated, the implant 300 may be configured to provide three points of contact Cp with the patient's bone B remaining from the broaching process along the anterior and posterior sides 302, 304 thereof. A first point of contact CP may be provided between the posterior side 304 of the implant 300 and the patient's bone B at the resection plane Rp, a second point of contact CP between the anterior side 302 of the implant 300 and the patient's bone B at the mid-body plane MBp and a third point of contact CP between the posterior side 304 of the implant 300 and the patient's bone B at distal to the three-quarter distal plane Dp in the region of the distal AP Tapers.

Thus arranged, by combining various features of the present disclosure (e.g., medial-lateral press-fit and anterior-posterior point of contacts), optimized placement and engagement of the implant 300 within the intramedullary canal IM of the patient's bone B has been discovered. That is, improved fit between the implant 300 and the patient's bone B has been discovered regardless of insertion approach and/or patient femur type.

In some embodiments, the implant 300 may also include a collar 350 (FIG. 9) extending from the medial side 306. In one preferred embodiment, the collar 350 does not wrap about the anterior and posterior sides 302, 304. By not wrapping the collar 350 about the anterior and posterior sides 302, 304, the implant 300 has been found to be more easily removed during a reversion surgery, if needed. Alternatively, the implant 300 could include any collar configuration now known or hereafter developed, or be configured as a collarless implant.

As described herein, in accordance with one or more features of the present disclosure, a femoral hip implant 300 arranged and configured with an optimized fit within the intramedullary canal IM of a patient's bone B is described. In accordance with features of the present disclosure, the implant 300 may be provided in a kit including, inter alia, a plurality of different sized implants thereby enabling the surgery to select the best fitting implant for the patient's bone B. Alternatively, the implant 300 may be patient-specific (e.g., utilizing scans of the patient's bone, the implant 300 may be specifically designed and manufactured for the patient).

In either event, with reference to FIGS. 12A-12F, in some embodiments, the implant 300 may be designed and configured by utilizing scans, such as, CT scans, across a population of patients or an individual patient if a patient-specific implant is being manufactured. Thereafter, patient specific scans may be taken, and those scans may then be evaluated to determine the gap or space between the outer surface of a selected implant 300 and the inner surface of the intramedullary canal IM of the patient's bone B. In accordance with features of the present disclosure, the gap or space is evaluated in both the medial-lateral direction and the anterior-posterior direction along specific cross-sections of the patient's bone B, which have been readily defined within literature such as, for example, the resection plane Rp, the mid-body plane MBp, and the distal plane Dp. Thus configured, the entire cross-sectional area of the intramedullary canal and the implant 300 is considered, which is contrary to conventional methodologies, which tend to emphasis only the medial-lateral fit (e.g., two dimensional templating studies observing fit in anterior-posterior and lateral radiographs without an understanding of the three dimensional fit within the femur).

In a preferred embodiment, the implant 300 is arranged and configured to fill a certain percentage of the cross-sectional area of the patient's intramedullary canal IM to reduce the likelihood of subsidence and avoid loosening. In preferred embodiments, the fill ratio or percentage can best be characterized as:

$$\text{Stem Fill Efficiency } (SFE) = \frac{\text{Subtracted Volume of } \textit{Cancelous} \text{ Bone } (SVC)}{\text{Stem Volume}}$$

As used herein, the volume of cancellous bone (SVC) is the volume of femoral bone whose density is differentiably lower than cortical bone. The subtracted volume of cancellous bone represents the volume of bone removed from the intermedullary canal through the broaching process. If the volume of the broach protrudes excessively into denser cortical bone, the volume of cancellous bone will be less than the volume of the broach and stem and the ratio will be less than one.

In use, the implant 300 is arranged and configured to fill the greatest proportion of the three-dimensional (3D) cross-sectional area of the patient's intramedullary canal IM with the least amount of interference with the patient's cortical bone. By minimizing the amount of cortical bone needing removal, ease of insertion is provided while still ensuring a good-fit between the implant 300 and the cortical bone B. In some embodiments, the SFE may be between $0.90 \leq SFE \leq 0.995$.

For example, in some embodiments, CT scans of the patient's bone B may be taken along various cross-sectional areas, which may be selected based on established cross-sectional areas defined within the art within established literature. Volumes of the patient's intramedullary canal IM can be measured or calculated using the scans. Thereafter, an optimized (e.g., best-fitting) implant 300 may be selected. Alternatively, in case of patient-specific implants, an implant 300 may be designed and manufactured via, for example, three-dimensional printing techniques. In either event, an optimized implant 300 based on the volume of the patient's intramedullary canal IM may be selected and implanted. That is, in selecting an optimized implant 300 for insertion into the patient's intramedullary canal IM, the implant 300 is evaluated and/or optimized in both the medial-lateral direction and the anterior-posterior direction (e.g., result is an implant 300 that has an increased fill ratio ensuring improved long-term stability of the implant 300 within the patient's intramedullary canal IM while avoiding excess bone removal during the broaching process).

Thus arranged, a femoral hip implant 300 may be selected to optimize fit within the patient's intramedullary canal IM while avoiding, or at least minimizing, the amount of cortical bone needing to be removed during the broaching process.

With reference to FIGS. 13-17, an embodiment of an orthopedic broach 400 in accordance with one or more features of the present disclosure is illustrated. In use, as will be readily appreciated by one of ordinary skill in the art, the orthopedic broach 400 may be utilized to prepare an intramedullary canal IM of a patient's bone B such as, for the patient's femur, to receive an orthopedic implant such as, for example, the hip stem implant 300 shown in FIGS. 8A-8E.

As previously described, the hip stem implant 300 may include a proximal region 310 and a distal region 330. In addition, the hip stem implant 300 includes an anterior side 302, a posterior side 304, a medial side 306, and a lateral side 308. As illustrated, in various embodiments, the proximal region 310 includes, and is defined by, a porous coated and/or roughened surface or region 320 (terms used interchangeably herein). In addition, within the porous coated region 320, the anterior and posterior sides 302, 304 include grooves 325 formed therein to facilitate improved engagement with the remaining patient's bone following the broaching process. As illustrated, in some embodiments, the grooves 325 are angled (e.g., angled downwards) along the anterior and posterior sides 302, 304 of the implant 300 from the lateral side 308 toward the medial side 306. In some embodiments, in accordance with one or more features of the present disclosure, the grooves 325 may extend to, and along, at least a portion of the medial side 306 of the hip stem implant 300.

As shown, in accordance with one or more features of the present disclosure, the broach 400 includes a body 401 having a proximal region 410 and a distal region 430. In addition, the body 401 includes an anterior side 402, a posterior side 404, a medial side 406, and a lateral side 408, wherein the anterior and posterior sides 402, 404 extend between the medial and lateral sides 406, 408 as will be appreciated by one of ordinary skill in the art. As illustrated, in use, the body 401 includes an outer surface having a size and shape substantially similar to the hip stem implant 300. As will be described in greater detail below, in accordance with one or more features of the present disclosure, the broach 400 includes differential teeth or tooth patterns. In one preferred embodiment, the broach 400 includes three different types of teeth including extraction or cutting teeth (e.g., diamond teeth), compaction teeth (e.g., annular teeth), and proximal-lateral teeth (e.g., chip-breakers or annular teeth with interrupted cuts).

Figure 18A:
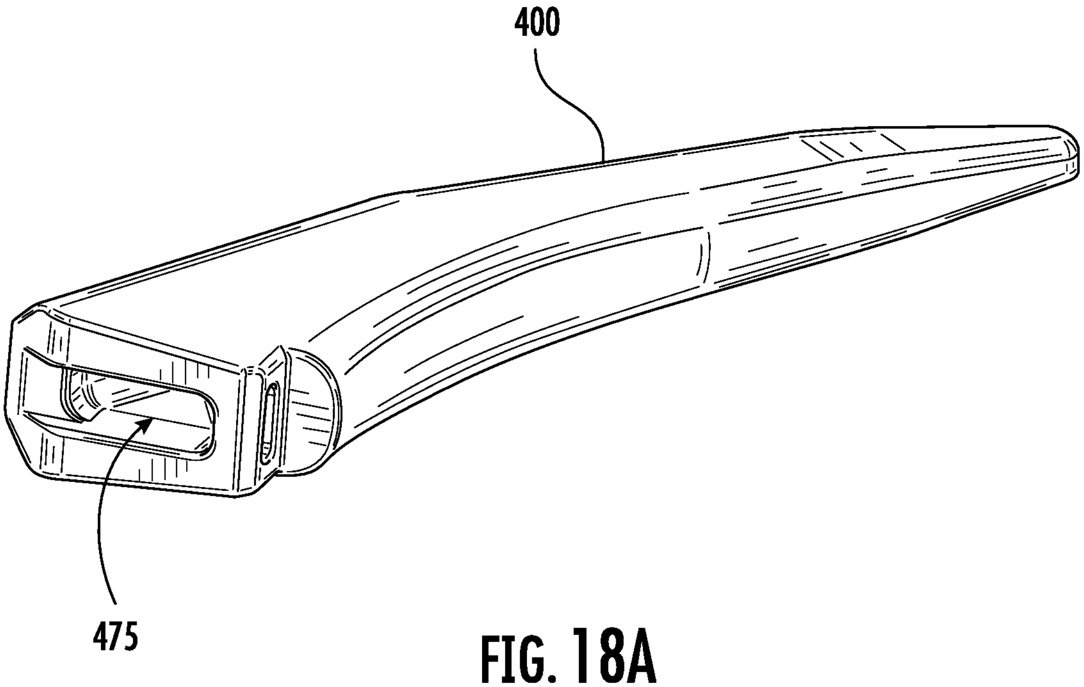
FIGS. 18A and 18B illustrate various views of an alternate embodiment of an orthopedic broach in accordance with one or more features of the present disclosure.
Figure 18B:
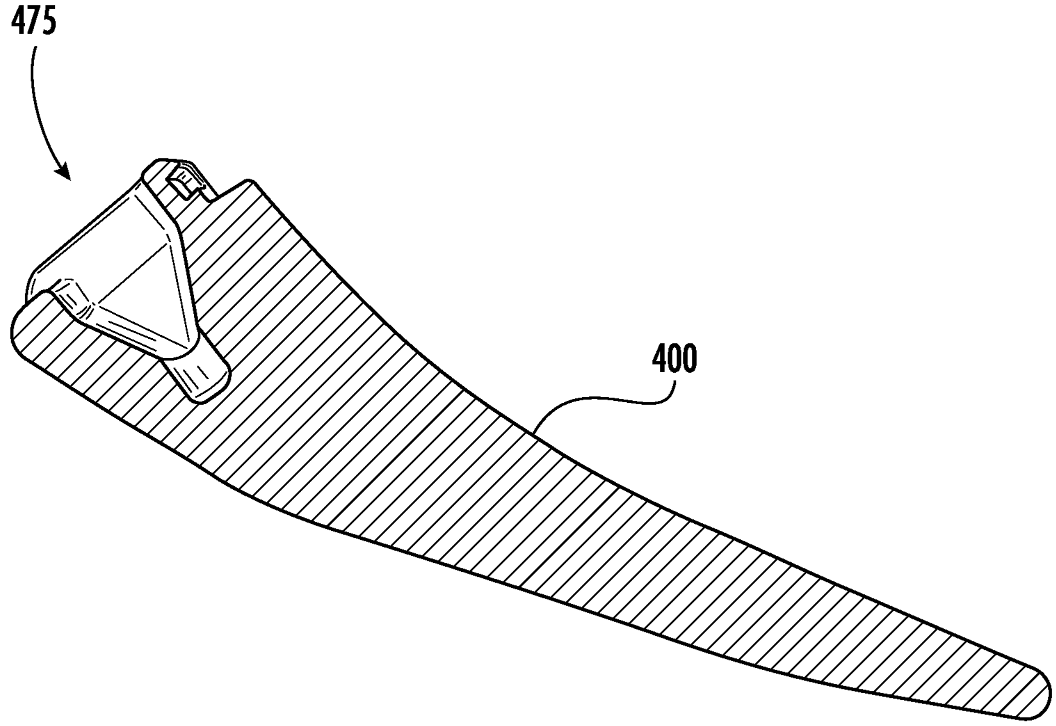

As illustrated in FIGS. 18A and 18B, in various embodiments, the body 401 includes a connection mechanism 475 arranged and configured to enable the broach 400 to be coupled to a handle, an orthopedic impactor, etc. In some embodiments, the connection mechanism 475 may be provided in the form of a cavity, a pocket, etc. Thus arranged, in use, the broach 400 does not interfere with preparation of the patient's acetabular. That is, in use, after the patient's femoral bone has been resected and the intramedullary canal broached, by utilizing a broach including a pocket or cavity as opposed to a post, the surgeon has more space or improved access to prepare the patient's acetabular (e.g., by utilizing a pocket or cavity there is no post to get in the way of the surgeon preparing the patient's acetabular). Alternatively, the connection mechanism 475 may be provided in the form of a post.

As illustrated, in some embodiments and as previously mentioned, the distal region 430 includes teeth 432 having a first tooth pattern. The proximal region 410 includes teeth 412 having a second tooth pattern and teeth 414 having a third tooth pattern. As illustrated, teeth 412 having the second tooth pattern may be positioned on the anterior, posterior, medial, and lateral sides 402, 404, 406, 408 while teeth 414 having the third tooth pattern are positioned on or adjacent to the medial and lateral surfaces 406, 408 (e.g., teeth 414 having the third tooth pattern are positioned along the corners, edges, or intersection between the anterior and posterior sides 402, 404 and the medial and lateral sides 406, 408). That is, the proximal region 410 may include teeth 414 having a third tooth pattern formed on the anteromedial, anterolateral, posteromedial and posterolateral aspects thereof.

Thus, as will be described in greater detail herein, in use, each of the first, second, and third tooth patterns is specifically arranged and configured, depending on its location, to optimize improved engagement of the prepared bone with the subsequently implanted hip stem implant 300 and/or implantation of the hip stem implant 300.

Figure 13:
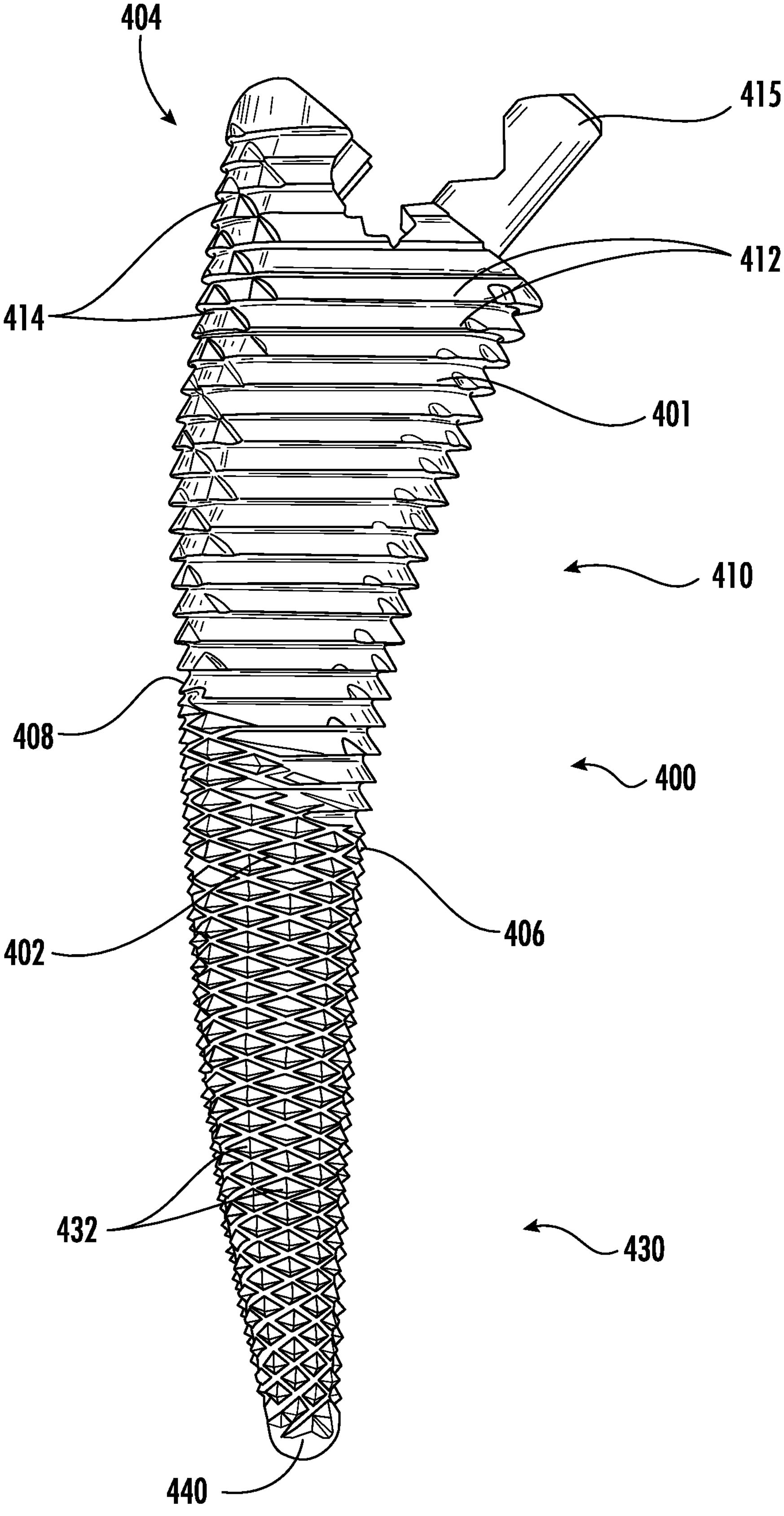
FIG. 13 is a side view of an example of an embodiment of an orthopedic broach that may be used in accordance with one or more features of the present disclosure.
Figure 14:
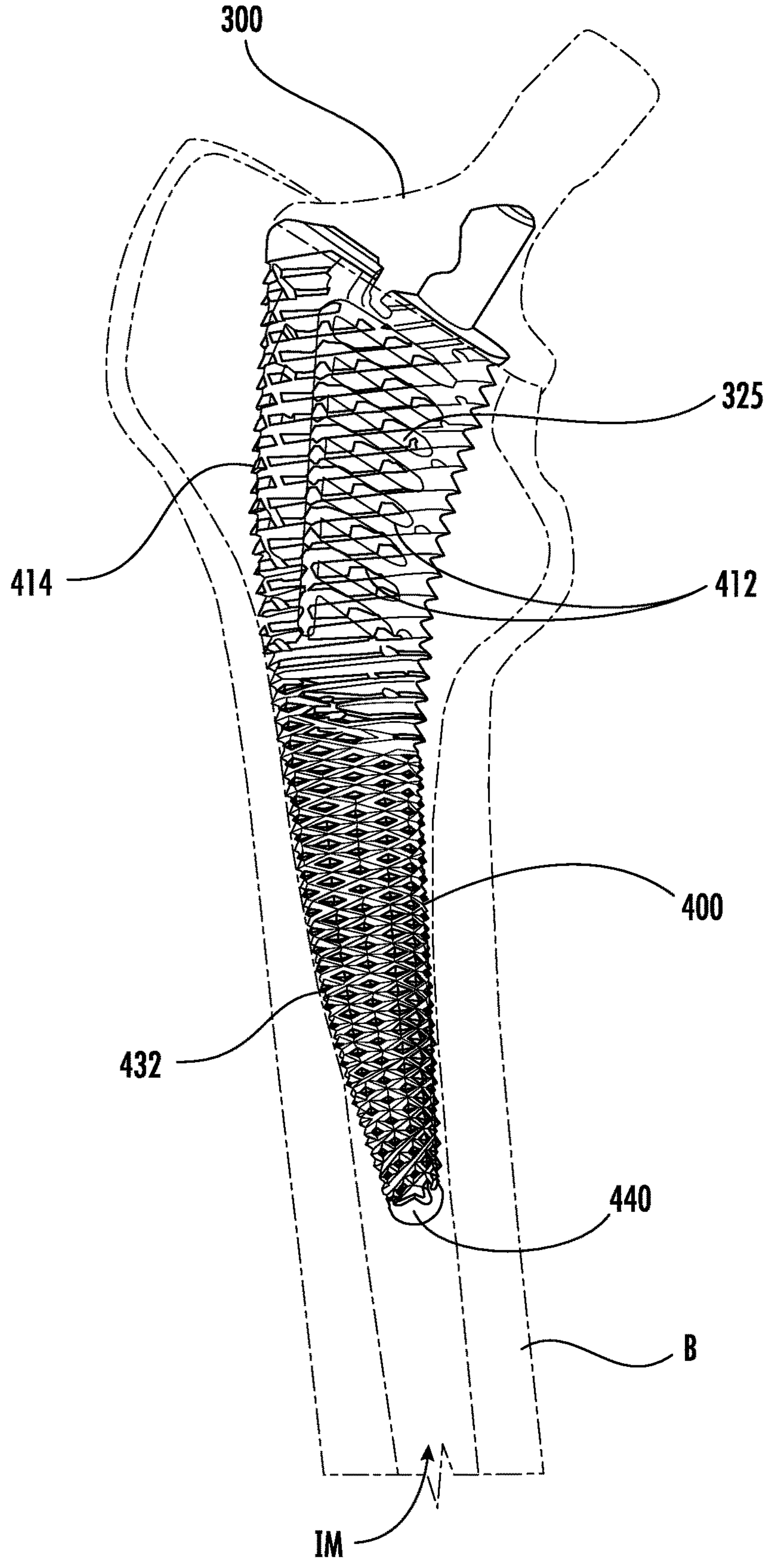
FIG. 14 is a perspective view of the orthopedic broach shown in FIG. 13 positioned within an intramedullary canal of a patient's bone, the orthopedic broach being overlaid on top of a femoral hip stem implant (FIGS. 8A-8E), which is also shown positioned within the intramedullary canal of the patient's bone.
Figure 15:
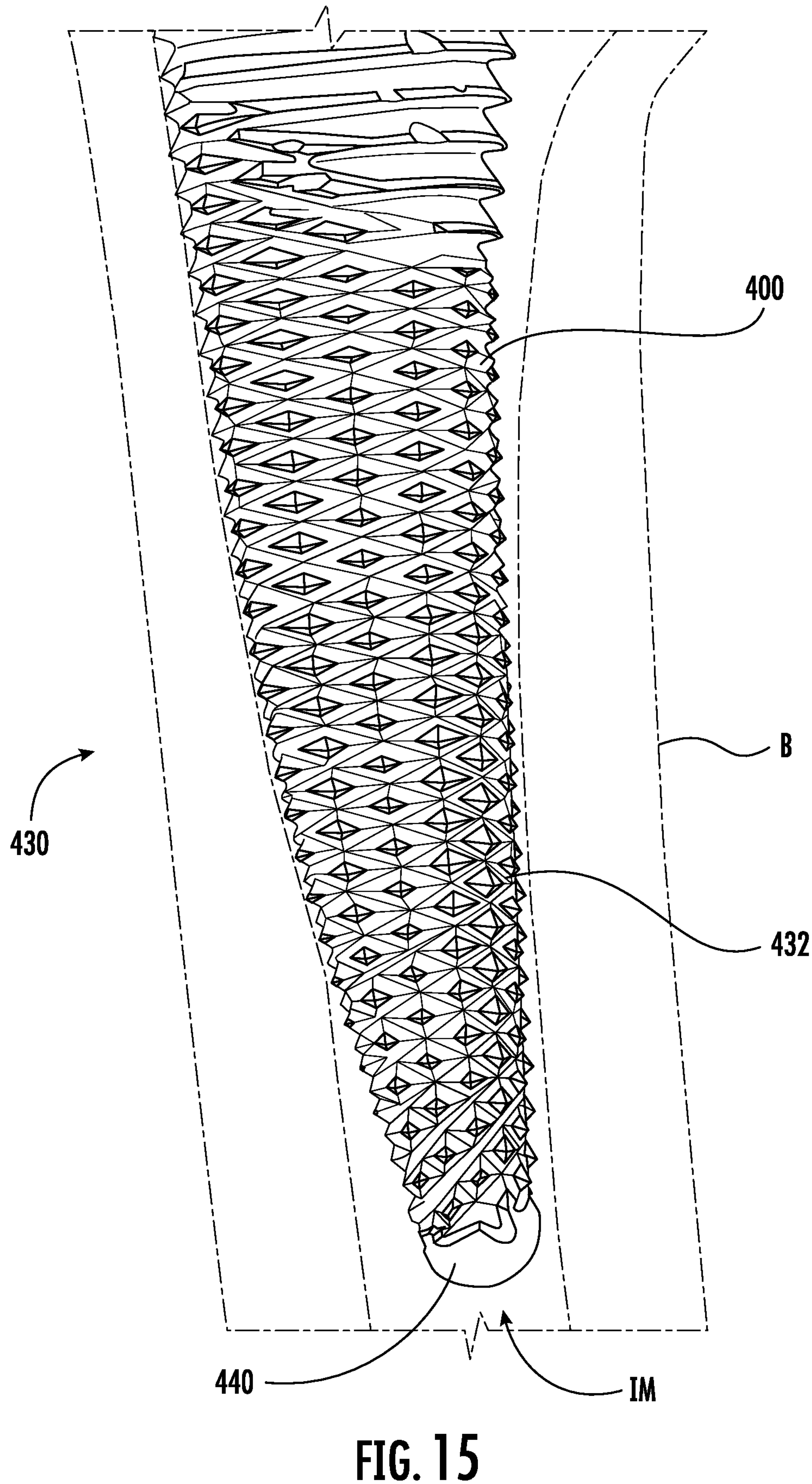
FIG. 15 is a detailed perspective view of a distal region of the orthopedic broach shown in FIG. 13 positioned within the intramedullary canal of the patient's bone.

Referring to FIGS. 13-15, as illustrated, the distal region 430 may terminate in a distal tip 440. As illustrated, in some embodiments, the teeth 432 formed on the distal region 430 of the broach 400 may extend all around (e.g., the teeth 432 may extend circumferentially about the distal region 430 on every side thereof). That is, the teeth 432 may be positioned on the anterior side 402, posterior side 404, medial side 406, and lateral side 408 of the distal region 430 of the broach 400, although this is but one configuration and other configurations are envisioned. As illustrated, in some embodiments, the distal tip 440 may be devoid of any teeth. Thus arranged, perforation of the patient's cortices by the distal tip 440 during broaching is minimized.

In addition, in some embodiments, the teeth 432 may be arranged and configured with a first tooth pattern that differs from the second and third tooth pattens, as will be described in greater detail below. In preferred embodiments, the teeth 432, or first tooth pattern, are pyramid or diamond shaped teeth arranged and configured to provide improved distal cutting of the patient's bone B upon insertion. Thus arranged, in use, the first tooth pattern (e.g., extraction teeth 432) formed on the distal region 430 of the broach 400 are arranged and configured to penetrate into and remove any bone that they come into contact with to create an envelope to facilitate proper positioning of the distal region 330 of the subsequently implanted hip stem implant 300 while avoiding bony fixation of the distal region 330 of the subsequently implanted hip stem implant 300 within the intramedullary canal. As such, the teeth 432 may be characterized as extraction or rasping teeth arranged and configured to cut or remove the patient's bone, and thus are optimized to remove diaphyseal bone. That is, in use, the pyramid or diamond shaped teeth 432 formed on the distal region 430 of the broach 400 optimizes the broach 400 to facilitate removal of any bone portions protruding on the inner surface of the intramedullary canal IM of the patient's bone B during insertion of the broach 400 therein (e.g., pyramid or diamond shaped teeth 432 have been found to perform better in reaming the patient's bone B as compared to other shaped teeth that have been found better to prepare the bone for press-fitting). In addition, in use, the blunt, diamond tooth pattern may provide a lower coefficient of friction with bone, which would provide an advantage for the portion of the broach intended to penetrate into the patient's tissue.

In use, the pyramid or diamond shaped teeth 432 formed on the distal region 430 of the broach 400 are arranged and configured to produce an envelope that minimizes or avoids press fit of the distal aspect or region 330 of the femoral hip stem implant 300 within the intramedullary canal to create a preferential press fit in the proximal portion 310 of the femoral hip stem implant 300 in the region corresponding to the anterior-posterior grooves 325 and porous coated region 320. That is, the distal region 430 of the broach 400 is patterned to remove bone leaving an envelope or a contact condition between the distal region 330 of the hip stem implant 300 that extends from the distal tip 340 of the hip stem implant 300 up to the termination of the porous coating 320 formed on the proximal region 310 of the hip stem implant 300. This transition is intended to avoid any kind of press fit condition with the distal region 330 of the hip stem implant 300 by providing a distal clearance between the inner surface of the patient's intramedullary canal and the distal region 330 of the subsequently implanted hip stem implant 300. In turn, this helps achieve and/or promote a proximal press fit hip stem implant 300 (e.g., loosely fitted distal region). As a result, excessive fit in long term on-growth, which may result in distal thigh pain or loosening of the distal stem due to proximal stem stress shielding can be avoided. Also, extending the pyramid or diamond shaped teeth 432 on the distal region 430 of the broach 400 allows for cortical bone removal at the mid-body of the hip stem implant 300, proximal to the isthmus and distal to the lesser trochanter.

Referring to FIGS. 13, 14, 16A-16E, and 17, as previously mentioned, the anterior, posterior, medial and lateral sides 402, 404, 406, 408 of the proximal region 410 of the broach 400 include teeth 412 having a second tooth pattern. That is, in accordance with one or more features of the present disclosure, the proximal region 410 formed on the broach 400 include teeth 412 having a second tooth pattern. In various embodiments, teeth 412 having a second tooth pattern can best be characterized as compaction teeth (e.g., teeth 412 arranged and configured to compact the bone on the inner surface of the intramedullary canal IM as opposed to cutting into it or removing it). In use, compaction teeth 412 are intended to leave larger particles of bone at the boney interface with greater penetration and densification of local boney tissue.

In use, the greater number and size of boney residue particles from the compaction teeth 412 provide greater degree of broaching residue such that the angled geometry of the anterior—posterior grooves create a generally positive rake angle to more effectively "peel" residue into the anterior and posterior grooves. This process is intended to provide the opportunity for osseoinduction into the anterior—posterior grooves to provide long term implant stability. Greater densification depth from the compaction teeth 412 is also intended to provide a firmer boney interface for initial femoral stem press-fit fixation.

In some embodiments, as illustrated, teeth 412 extend horizontally across the anterior, posterior, medial and lateral sides 402, 404, 406, 408 of the proximal region 410 of the broach 400. For example, as illustrated, the teeth 412 may extend horizontally across the anterior and posterior sides 402, 404 between the medial and lateral sides 406, 408 (e.g., teeth 412 include, or form, annular, parallel ledges or steps). The teeth 412 are arranged and configured as annular teeth extending horizontally between the medial and lateral sides 406, 408 of the broach 400. The annular teeth 412 being configured as compaction teeth to enable bone preservation and stability. In use, during insertion of the broach 400 into the patient's intramedullary canal IM, the proximal annular teeth 412 pushes or compacts the patient's bone (e.g., compacts or moves the patient's bone to make an improved envelope for subsequent implantation of the hip stem implant 300).

In addition, in accordance with one or more features of the present disclosure, the proximal region 410 formed on the broach 400 including teeth 412 having the second tooth pattern has a shape and location that substantially matches or mimics the porous coated region 320 formed on the proximal region 310 of the hip stem implant 300. Thus arranged, the proximal region 410 of the broach 400 mimics or matches the porous coated region 320 of the hip stem implant 300 (e.g., the placement of the teeth 412 having the second tooth pattern mimics or matches the placement of the porous coated region 320 on the hip stem implant 300). That is, the proximal region 410 formed on the broach 400 include teeth 412 having the second tooth pattern is identical, or substantially identical, to the porous coated region 320 formed on the hip stem implant 300.

In use, during insertion of the broach 400, the proximal annular teeth 412 leave a pocket in the patient's bone arranged and configured to interact with the porous coated region 320 and the anterior-posterior grooves 325 formed on the hip stem implant 300. That is, the proximal annular teeth 412 are arranged and configured to compact and move the contacted bone while also leaving some cancellous bone to engage the porous coated region 320 and the anterior-posterior grooves 325 formed on the subsequently implanted hip stem implant 300.

Figure 17:
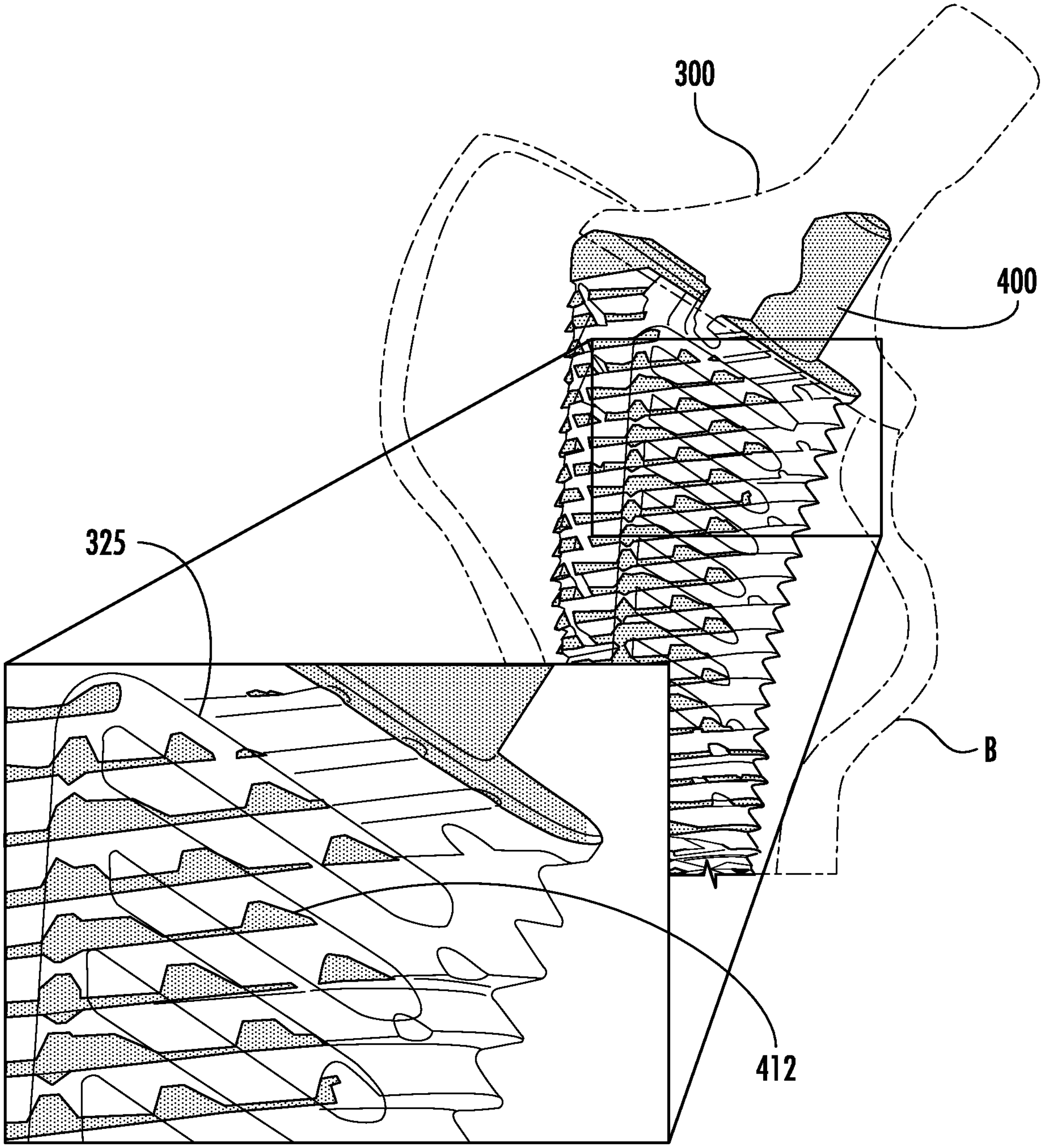
FIG. 17 illustrates alternate detailed views of a proximal region of the orthopedic broach shown in FIG. 13.

As best illustrated in FIGS. 14 and 17, the annular teeth 412 formed on the broach 400 form horizontally extending, parallel ridges in the patient's bone (e.g., the proximal anterior and posterior annular tooth pattern is generally perpendicularly arranged relative to a longitudinal axis of the subsequently implanted hip stem implant 300), which are angled relative to the anterior-posterior grooves 325 formed on the subsequently implanted hip stem implant 300. Thus arranged, perpendicularly arranged annular teeth 412 on the broach 400 compact and/or densify the cancellous bone leaving a slight stair-step pattern. The corresponding opposing anterior and posterior sides 302, 304 of the subsequently implanted hip stem implant 300 includes grooves 325 that are angled with respect to the arrangement of the perpendicularly arranged annular compaction teeth 412 on the broach 400 thereby producing a cross-hatching pattern as will be described in greater detail below. Thus arranged, implantation of the hip stem implant 300 causes the implant 300 to scrap the peaks of the stair-step cavity (e.g., parallel ridges) left behind from the broaching process into the recess of the grooves 325 formed on the anterior and posterior sides 302, 304 of the hip stem implant 300 providing accelerated bony in-growth and resulting in increased resistance to subsidence and rotational micromotion.

That is, the parallel ridges formed on the patient's intramedullary cavity IM by the broaching process can be subsequently raked during implantation of the hip stem implant 300 (e.g., implantation of the hip stem implant 300 with anterior-posterior grooves 325 rake the patient's inner surface of the intramedullary canal IM again), which has been found to minimize any gaps that may remain between the raked bone and the anterior-posterior grooves 325 in the hip stem implant 300 thereby facilitating improved long term stability.

Thus, in accordance with one or more features of the present disclosure, by matching or aligning the porous coated region 320 of the hip stem implant 300 with the annular compaction teeth 412 formed on the proximal region 410 of the broach 400, the interface between the hip stem implant 300 and the patient's bone (cortical/cancellous) is addressed. The result is to compact and densify the bony apposition to the porous coated region 320 formed on the subsequently implanted hip stem implant 300 while clearing the diaphysis of the intramedullary canal of the patient's bone to contact/support the distal region 330 of the hip stem implant 300 without a press fit. Thereby, allowing a differential press fit to the proximal in-growth surface on the hip stem implant 300 and avoiding a distal "pedastool" or press fit which may lead to long term stress shielding of the proximal femur and implant loosening.

Figure 16A:
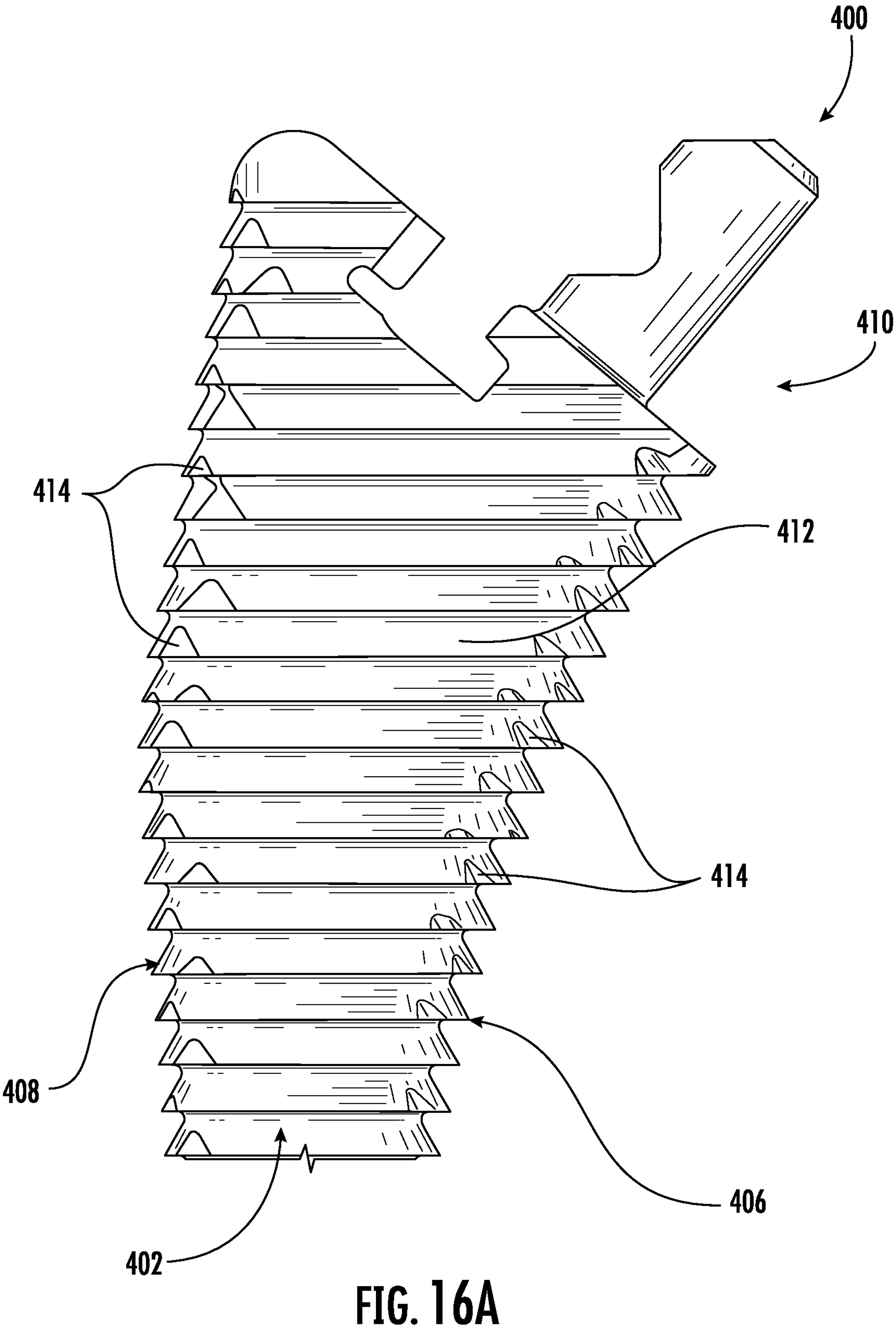
FIGS. 16A-16E are detailed views of a proximal region of the orthopedic broach shown in FIG. 13, FIGS. 16A-16E illustrating the configuration and layout of teeth having a third tooth pattern.
Figure 16B:
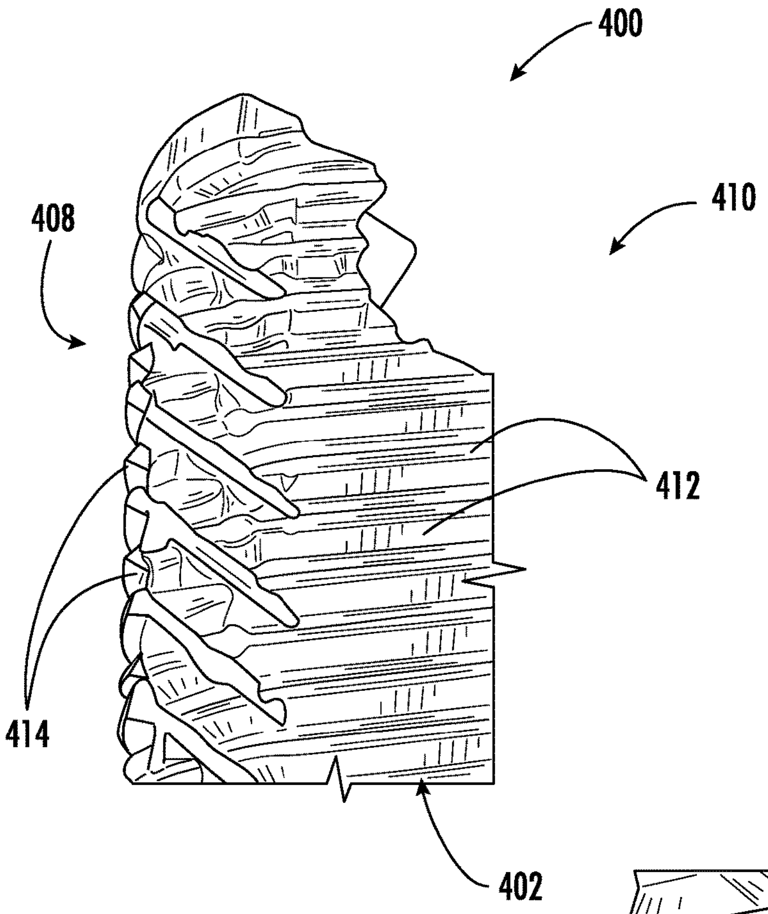
Figure 16C:
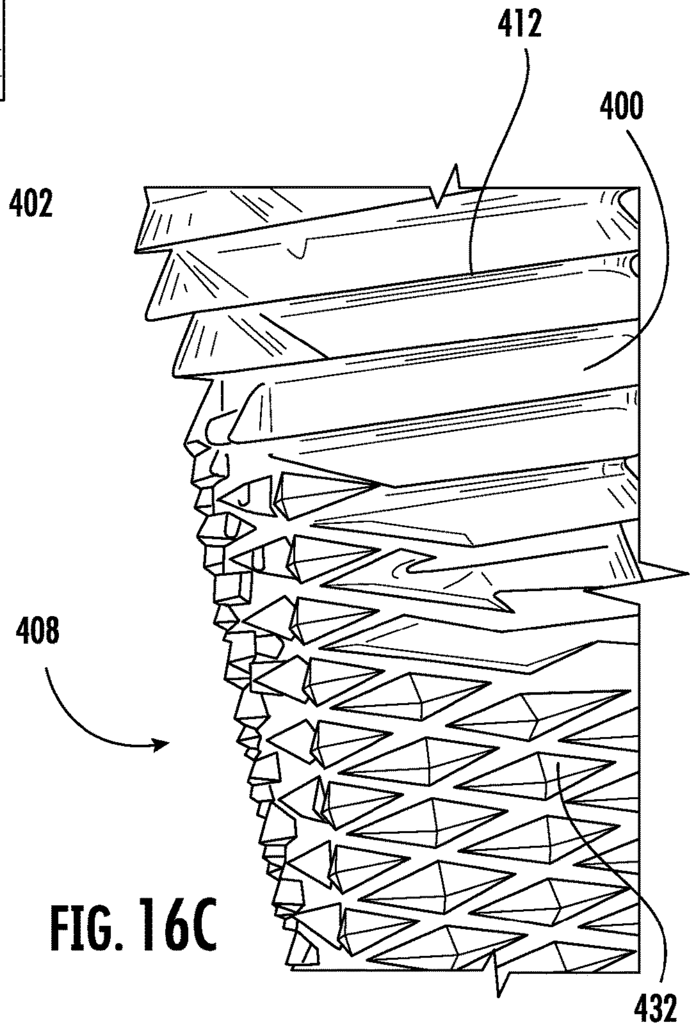
Figure 16D:
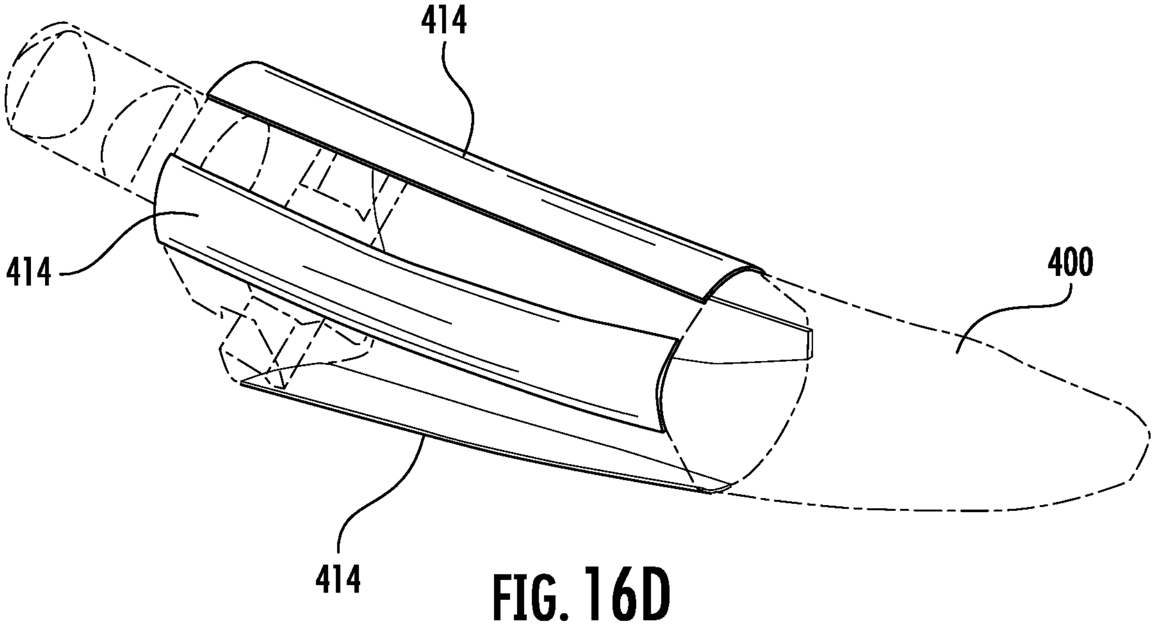
Figure 16E:
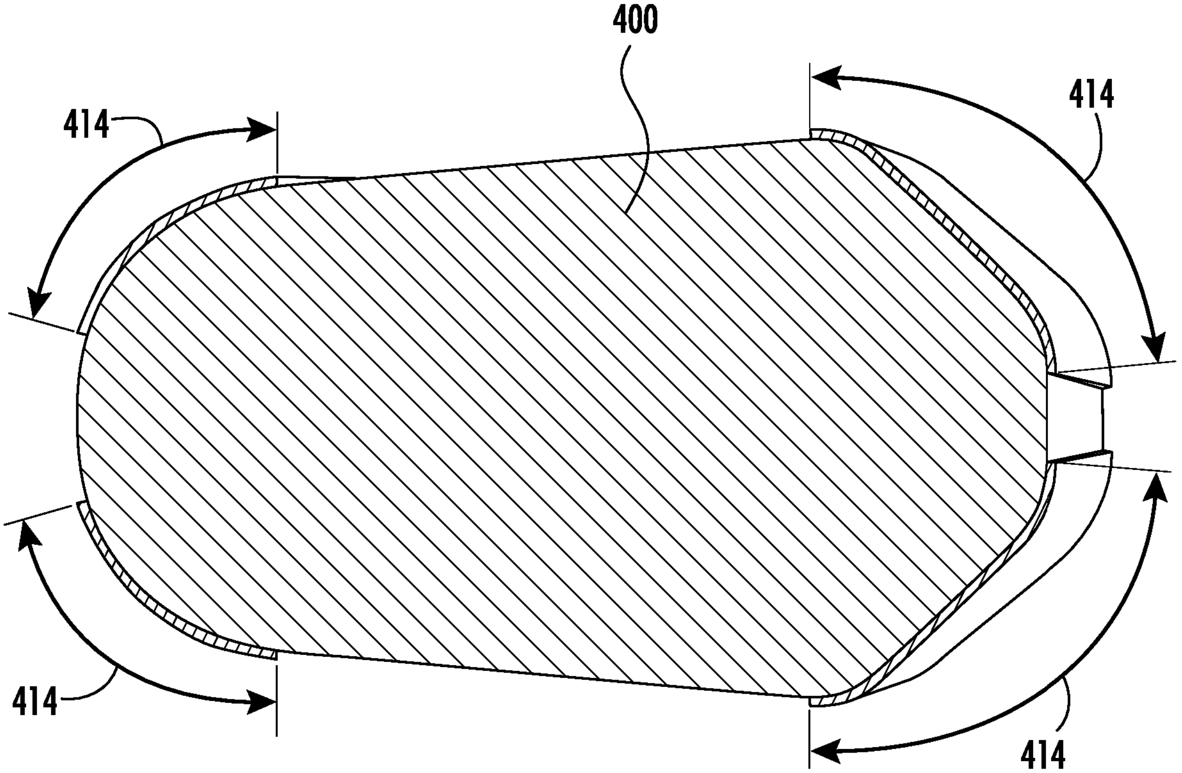

As best illustrated in FIGS. 13, 14, and 16A-16E, in accordance with one or more features of the present disclosure, and as previously mentioned, the medial and lateral sides 406, 408 of the proximal region 410 of the broach 400 include teeth 414 having a third tooth pattern (e.g., teeth 414 having the third tooth pattern are positioned along the corners, edges, or intersection between the anterior and posterior sides 402, 404 and the medial and lateral sides 406, 408). More specifically, with reference to FIGS. 16A-16E, the proximal region 410 may include teeth 414 having a third tooth pattern formed on the anteromedial, anterolateral, posteromedial and posterolateral aspects thereof as schematically illustrated in FIGS. 16D and 16E. Location of the third tooth pattern is arranged and configured to correspond to the proximal press-fit section of the same-sized femoral stem in the antero- and postero-medial and lateral aspects or regions as schematically shown in FIGS. 16D and 16E. In use, the third tooth pattern may be arranged as horizontal teeth with an angled "cutting flute" relief passing through for effective removal of boney residue intended to preferentially achieve press fit away from the adjacent bone at the "corners" of the broach where anterior, posterior, medial and lateral bone of greater surface density to achieve an optimized or preferential press fit in the corresponding region of the hip stem implant.

In some embodiments, the teeth 414, or third tooth pattern, are arranged and configured as corner teeth to cut and/or remove the patient's bone that contacts the teeth during broaching. As such, the teeth 414 may be referred to as cutting teeth, extraction teeth, or chip-breakers, which are arranged and configured to cut into the patient's bone (e.g., optimized to remove cancellous bone). In some embodiments, as illustrated, the teeth 414, or third tooth pattern, are arranged and configured to provide the proximal-lateral region with interrupted cuts to create or provide a press fit in the corresponding proximal-lateral region of the subsequently implanted hip stem implant 300 while also providing reduced densification of the bone. The interrupted cuts facilitate a path for bone extrusion during broaching and a more aggressive pattern that allows relief of proximal cortical bone in the patient's femur. As illustrated, the teeth 414 may be configured to provide an annular grind, while incorporating a relief to allow material to flow out during the broaching process.

Thus arranged, in use, the teeth 414 are arranged and configured to extract the patient's bone on the medial and lateral sides of the intramedullary canal of the patient's bone. In particular, the teeth 414, or third tooth pattern, are arranged and configured to extract or remove any bone on the lateral side of the intramedullary canal on the patient's bone to promote clearance (e.g., prevent lateralization, which may cause the broach to be inserted crooked (e.g., at an angle)). As such, the teeth 414 facilitate clearance during implantation of the hip stem implant 300 by preventing, or at least minimizing, lateralization.

In accordance with features of the present disclosure, with reference to FIG. 17, post broaching with the hip stem implant 300 positioned within the intramedullary canal IM of the patient's bone B, the teeth 412 formed on the proximal region 410 of the broach 400 are arranged and configured to form a cross-hatching with the grooves 325 formed on the anterior and posterior sides 302, 304 of the hip stem implant 300. Thus arranged, the annular teeth 412 are configured to push the patient's bone on the anterior and posterior sides of the patient's intramedullary canal, which, during implantation of the hip stem implant 300, rakes the patient's bone creating an improved envelope for receiving the stem of the hip stem implant 300 while leaving pockets for the grooves 325 formed on the hip stem implant 300 to fill with bone-in-growth (e.g., ridges are left in the patient's bone that can be scrapped by the grooves 325 formed on the hip stem implant 300 eliminating, or at least minimizing, any gap that bone needs to bridge).

While particular embodiments of the orthopedic broach have been shown and described, alternative configurations are envisioned. For example, in some embodiments, reduction or enlargement of the broaching surfaces can be provided to enable differential press fit with the opposing surfaces formed on the hip stem implant. In some embodiments, this may include gradual drafting of the surface(s) or direct offsets. This may also be achieved by differential coating thickness formed on the hip stem implant to create a targeted press fit potentially relating to gruene zones historically known to resorb due to stress shielding. In addition, and/or alternatively, it is envisioned that additional interrupted cuts may be provided distally on the diamond shaped tooth pattern to remove bone along the medial and lateral sides of the distal region.

In summary, in various embodiments, in accordance with one or more features of the present disclosure, the broach includes a differential tooth pattern including first, second, and third different tooth patterns wherein the broach includes (i) proximal compaction teeth along the anterior and posterior sides thereof to facilitate an envelope densification, (ii) extraction teeth formed along the corners of the proximal region to facilitate chip breakers/flutes, and (iii) distal extraction teeth to clear cortical bone. Thus arranged, the broach is optimized to provide a proximal press fitted hip stem implant, which establishes a crossing pattern between the ridges formed on the patient's intramedullary canal by the proximal annular teeth and the anterior-posterior grooves formed on the hip stem implant to promote raking of the bone during implantation of the hip stem implant into the grooves.

The femoral hip implant may be manufactured from any suitable biocompatible material now known or hereafter developed used to manufacture orthopedic implants. For example, the femoral hip implant may be made from cobalt chromium, stainless steel, titanium, oxidized zirconium, or other metal alloys. Alternatively, the femoral hip implant may be manufactured from standard polyethylene, cross-linked polyethylene, ultra-high molecular weight plastic, other plastics, ceramics, or a composite material. Similarly, the broach may be manufactured from any suitable material now known or hereafter developed. For example, the broach may be manufactured entirely from stainless steel. Alternatively, other metals may be used. Additionally, in some embodiments, the broach may be made from a hard plastic, such as PEEK.

The femoral hip implant and broach may be formed using any desired or appropriate methodologies or technologies now known or hereafter developed. For example, in some embodiments, the femoral hip implant and broach may be manufactured using any now known or hereafter developed additive manufacturing technique. By way of some, non-limiting known techniques, the femoral hip implant and broach could be manufactured from selective laser sintering (SLS), direct metal laser sintering (DMLS), electron beam melting (EBM), selective laser melting (SLM), three-dimensional printing, or the like. For instance, in some embodiments, the entire femoral hip implant and broach may be formed as a monolithic or integral component (including any porous or other in-growth promoting surfaces or materials formed on the implant). In some embodiments, portions of the femoral hip implant may be formed and then additional in-growth materials, surfaces, and/or treatments could be added or applied to the implant. In other embodiments, an additive manufacturing technique such as, for example, electron beam melting methods or methods that use lasers to subtract or remove select portions of material from an initially solid material may be used. In other embodiments, portions or all of the femoral hip implant and broach can be formed using casting or other technologies or methods. In some embodiments, a non-porous implant such as a femoral hip implant may be formed using an additive manufacturing technique such as, for example, SLS technologies and subsequently that implant may be subjected to acid etching, grit blasting, plasma spraying (e.g., of titanium oxide or another metal to promote in-growth) or other treatments.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Any embodiment or feature of any section, portion, or any other component shown or particularly described in relation to various embodiments of similar sections, portions, or components herein may be interchangeably applied to any other similar embodiment or feature shown or described herein. Additionally, components with the same name may be the same or different, and one of ordinary skill in the art would understand each component could be modified in a similar fashion or substituted to perform the same function.

Moreover, the following claims are hereby incorporated into this Detailed Description by this reference, with each claim standing on its own as a separate embodiment of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

We claim:

1. A femoral hip stem kit comprising:

a hip stem implant configured to be implanted within an intramedullary canal, the hip stem implant including a proximal region, a distal region, an anterior side, a posterior side, a medial side, and a lateral side, the proximal region including a porous coated surface applied thereto; and an orthopedic broach used to prepare the intramedullary canal for receipt of the hip stem implant, the broach including a proximal region, a distal region, an anterior side, a posterior side, a medial side, and a lateral side, the broach including a plurality of uniquely arranged tooth patterns formed thereon, the plurality of uniquely arranged tooth patterns including compaction teeth having a tooth pattern formed on the proximal region thereof and extraction teeth having a tooth pattern formed on the distal region thereof arranged and configured to cut or remove the patient's bone, wherein the tooth pattern of the compaction teeth is different than the tooth pattern of the extraction teeth; and wherein the proximal region of the broach including the compaction teeth is sized and configured to mimic a size and configuration of the porous coated surface formed on the hip stem implant.

2. The system of claim 1, wherein the proximal region of the broach including the compaction teeth has a shape and location and the porous coated surface defining the proximal region of the hip stem implant has a shape and location, the shape and location of the proximal region of the broach including the compaction teeth having the same shape and location as the porous coated surface formed on the proximal region of the hip stem implant.

3. The system of claim 1, wherein the proximal region of the hip stem implant includes a plurality of grooves formed on the anterior and posterior sides thereof, the grooves formed on the anterior side wrapping around a corner onto the medial side.

4. The system of claim 3, wherein the grooves formed on the anterior and posterior sides of the hip stem implant are angled relative to a longitudinal axis of the hip stem implant.

5. The system of claim 4, wherein the compaction teeth formed on the anterior and posterior sides of the broach are arranged and configured as annular teeth extending perpendicularly relative to a longitudinal axis of the broach so that the compaction teeth are angled relative to the grooves formed on the anterior and posterior sides of the hip stem implant.

6. The system of claim 5, wherein the compaction teeth extend horizontally from the lateral side to medial side of the broach.

7. The system of claim 1, wherein the plurality of uniquely arranged tooth patterns further include:

a plurality of extraction teeth formed on anteromedial, anterolateral, posteromedial, and posterolateral aspects of the proximal region of the broach.

8. The system of claim 7, wherein the plurality of extraction teeth formed on the distal region of the broach includes diamond or pyramid shaped teeth.

9. The system of claim 8, wherein the plurality of extraction teeth formed on the medial and lateral sides of the proximal region of the broach define interrupted cuts formed along edges of the medial and lateral sides of the broach.

10. The system of claim 1, wherein the broach includes a connection mechanism, the connection mechanism configured as a cavity for receiving a male component.

11. The system of claim 1, wherein the anterior side and the posterior side of the hip stem implant are tapered towards a central longitudinal axis of the hip stem implant.

12. The system of claim 11, wherein the hip stem implant includes a dual-tapered anterior-posterior taper arrangement including a first anterior-posterior taper extending from a shoulder to a transition point and a second anterior-posterior taper extending from the transition point towards a distal tip, the second anterior-posterior taper being different than the first anterior-posterior taper.

13. The system of claim 1, wherein the medial side of the proximal region of the hip stem implant includes a constant arc of curvature configured to provide a press-fit.

14. A femoral hip stem kit comprising:

a hip stem implant configured to be implanted within an intramedullary canal, the hip stem implant including a proximal region, a distal region, an anterior side, a posterior side, a medial side, and a lateral side, the proximal region including a porous coated surface applied thereto; and an orthopedic broach used to prepare the intramedullary canal for receipt of the hip stem implant, the broach including a proximal region, a distal region, an anterior side, a posterior side, a medial side, and a lateral side, the broach including a plurality of uniquely arranged tooth patterns formed thereon, the plurality of uniquely arranged tooth patterns including compaction teeth having a tooth pattern formed on the proximal region thereof and extraction teeth having a tooth pattern formed on the distal region thereof arranged and configured to cut or remove the patient's bone, wherein the tooth pattern of the compaction teeth is different than the tooth pattern of the extraction teeth;

wherein the proximal region of the broach including the compaction teeth is sized and configured to mimic a size and configuration of the porous coated surface formed on the hip stem implant; and wherein the compaction teeth are positioned entirely in a first configuration and the porous coated surface is positioned entirely in a second configuration, the first configuration matching the second configuration.

15. The system of claim 14, wherein the proximal region of the broach including the compaction teeth has a shape and location and the porous coated surface defining the proximal region of the hip stem implant has a shape and location, the shape and location of the proximal region of the broach including the compaction teeth having the same shape and location as the porous coated surface formed on the proximal region of the hip stem implant.

16. The system of claim 14, wherein the proximal region of the hip stem implant includes a plurality of grooves formed on the anterior and posterior sides thereof, the grooves formed on the anterior side wrapping around a corner onto the medial side.

17. The system of claim 16, wherein the grooves formed on the anterior and posterior sides of the hip stem implant are angled relative to a longitudinal axis of the hip stem implant.

18. The system of claim 17, wherein the compaction teeth formed on the anterior and posterior sides of the broach are arranged and configured as annular teeth extending perpendicularly relative to a longitudinal axis of the broach so that the compaction teeth are angled relative to the grooves formed on the anterior and posterior sides of the hip stem implant.

19. The system of claim 14, wherein the plurality of uniquely arranged tooth patterns further include:

a plurality of extraction teeth formed on anteromedial, anterolateral, posteromedial, and posterolateral aspects of the proximal region of the broach.

20. The system of claim 19, wherein the plurality of extraction teeth formed on the distal region of the broach includes diamond or pyramid shaped teeth.

* * * * *